US008614054B2

(12) United States Patent
Davis et al.

(10) Patent No.: US 8,614,054 B2
(45) Date of Patent: Dec. 24, 2013

(54) LASER SCANNING CYTOMETRY MEDIATED ANALYSIS OF THERAPEUTIC EFFICACY IN TUMORS

(75) Inventors: Darren W. Davis, La Porte, TX (US); David J McConkey, Bellaire, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1520 days.

(21) Appl. No.: 12/024,562

(22) Filed: Feb. 1, 2008

(65) Prior Publication Data

US 2011/0236909 A1    Sep. 29, 2011

Related U.S. Application Data

(63) Continuation of application No. 10/145,275, filed on May 14, 2002, now abandoned, which is a continuation of application No. PCT/US01/43860, filed on Nov. 6, 2001.

(60) Provisional application No. 60/246,279, filed on Nov. 6, 2000.

(51) Int. Cl.
*G01N 1/30* (2006.01)
*G01N 33/567* (2006.01)
*G01N 33/574* (2006.01)
*C12N 9/10* (2006.01)

(52) U.S. Cl.
USPC .......... 435/4; 435/7.21; 435/7.23; 435/40.52; 435/193

(58) Field of Classification Search
None
See application file for complete search history.

(56) References Cited

U.S. PATENT DOCUMENTS

| | | | |
|---|---|---|---|
| 5,427,910 A | 6/1995 | Kamentsky et al. | 435/6 |
| 5,616,469 A | 4/1997 | Brawer | 435/7.23 |
| 5,688,694 A | 11/1997 | Brawer | 436/64 |
| 5,793,969 A | 8/1998 | Kamentsky et al. | 395/200.43 |
| 5,840,507 A | 11/1998 | Fruehauf | 435/7.23 |
| 5,885,840 A | 3/1999 | Kamentsky et al. | 436/63 |
| 5,942,385 A | 8/1999 | Hirth | 435/4 |
| 6,009,342 A | 12/1999 | Brasch et al. | 600/420 |
| 6,656,683 B1 * | 12/2003 | Reuben et al. | 435/6.14 |

FOREIGN PATENT DOCUMENTS

WO    WO 00/26368    5/2000

OTHER PUBLICATIONS

Dowsett et al (Primary Medical Therapy for Breast Cancer, ESO Updates, vol. 4, Aug. 1999, pp. 113-125).*
Dowsett, (Award No. DAMD17-97-1-7335, Sep. 1999).*
Ben-Hur et al (Journal of Neuroscience, 1998, vol. 18, pp. 5777-5788).*

Bender (Cytometry, Mar. 1, 1999, vol. 35, pp. 181-195).*
Advisory Action issued by United States Patent and Trademark Office in U.S. Appl. No. 10/145,275, mailed May 31, 2007.
Arap et al., "Cancer treatment by targeted drug delivery to tumor vasculature in a mouse model", *Science*, 279: 377-380, 1998.
Bergers et al., "Effects of angiogenesis inhibitors on multistage carcinogenesis in mice," *Science*, 284: 808-812, 1999.
Blankenberg et al., "In vivo detection and imaging of phosphatidylserine expression during programmed cell death," *Proc Natl Acad Sci USA.*, 95: 6349-6354, 1998.
Clatch et al., "Immunophenotypic analysis of hematologic malignancy by laser scanning cytometry," *Am J Clin Pathol*, 105:744-755, 1996.
Clatch et al., "Simplified immunophenotypic analysis by laser scanning cytometry," *Cytometry*, 34:3-16, 1998.
Cosgrove et al., "Color Doppler signals from breast tumors. Work in progress" *Radiology*, 176:175-180, 1990.
Darzynkiewicz and Bedner, "Analysis of Apoptotic Cells by Flow and Laser Scanning Cytometry," *Methods Enzymol.*, 322:18-39, 2000.
Dong et al., "Bax and apoptosis in acute and chronic rejection of rat cardiac allografts" *Lab Invest.*, 79:1643-1653, 1999.
Drevs et al., "Effects of PTK787/ZK 222584, a Specific Inhibitor of Vascular Endothelial Growth Factor Receptor Tyrosine Kinases, on Primary Tumor, Metastasis, Vessel Density, and Blood Flow in a Murine Renal Cell Carcinoma Model," *Cancer Res.*, 60:4819-4824, 2000.
Eberhard et al., "Heterogeneity of angiogenesis and blood vessel maturation in human tumors: Implications for antiangiogenic tumor therapies," *Cancer Res.*, 60:1388-1393, 2000.
Fanelli et al., "Assessment of tumor vascularization: immunohistochemical and non-invasive methods" *Int. J. Biol. Markers*, 14:218-231, 1999.
Folkman et. al., "Angiogenic factors," *Science*, 235:442-447, 1987.
Fox et al., "Quantitation and prognostic value of breast cancer angiogenesis: comparison of microvessel denstiy, Chalkley count,and computer image analysis" *J. Pathol*, 177: 275-283, 1995.
Friedlander et al., "Definition of two angiogenic pathways by distinct alpha v integrins," *Science*, 270: 1500-1502, 1995.
Gavrieli et al., "Identification of programmed cell death in situ via specific labeling of nuclear DNA fragmentation," *J. Cell Biol.*, 119:493-501, 1992.
Gazit et al., "Fractal characteristics of tumor vascular architecture during tumor growth and regression," *Microcirculation*, 4:395-402, 1997.
Germain et al., "Use of a biotinyl-estradiol derivative to demonstrate estradiol-membrane binding sites on adherent human breast cancer MCF-7 cells," *Anticancer Res.*, 13:2347-2354, 1993.

(Continued)

*Primary Examiner* — Karen Canella
(74) *Attorney, Agent, or Firm* — Parker Highlander PLLC

(57) ABSTRACT

This invention describes the use of a laser scanning device, for example a laser scanning CYTOMETRY (LSC), with a double-fluorescent labeling technique as a quantitative method that can be used to objectively and accurately measure endothelial cell death, endothelial tumor cell death and blood vessel density of tumor tissue. These parameters can be used as markers of efficacy in tumors treated with anti-angiogenic or traditional therapies and can distinguish patients who respond to these drugs from those who do not.

48 Claims, 23 Drawing Sheets
(5 of 23 Drawing Sheet(s) Filed in Color)

(56) References Cited

OTHER PUBLICATIONS

Gorczyca et al., "Analysis of Apoptosis in Solid Tumors by Laser-Scanning Cytometry," *Mod.* Pathology, 11:1052-1058, 1998.
Gorczyca et al., "Analysis of human tumors by laser scanning cytometry," *Methods in Cell Biol.*, 64:421-443, 2001.
Granville et al., "Release of cytochrome c, Bax migration, Bid cleavage, and activation of caspases 2, 3, 6, 7, 8, and 9 during endothelial cell apoptosis," *Amer. J. Pathol.*, 155(4):1021-1025, 1999.
Grasl-Kraupp et al., "In situ detection of fragmented DNA (TUNEL assay) fails to discriminate among apoptosis, necrosis, and autolytic cell death: a cautionary note," *Hepatology*, 21:1465-1468, 1995.
Griffey et al., "Computer-assisted image analysis of intratumoral vessel density in mammary tumors from dogs" *Am. J. Vet Res.*, 59:1238-1242, 1998.
Herbst et al., "A Phase I Clinical Trial of Recombinant Human Endostatin (rHE) in Patients (PTS) with Solid Tumors: Surrogate Analyses to Determine a Biologically Effective Does (BED)," *Proceedings of the American Association for Cancer Research Annual*, 42:382, 2001 (Abstract #4469).
Ikeda et al., "Massive apoptosis detected by in situ DNA nick end labeling in neuroblastoma" *Am J. Surg. Pathol*, 20:649-655, 1996.
International Preliminary Examination Report issued by IPEA/US in PCT/US01/43860, completed Sep. 13, 2004.
International Search Report issued by ISA—European Patent Office in PCT/US01/43860, mailed Sep. 30, 2002.
Kamentsky and Kamentsky, "Microscope-based multiparameter laser scanning cytometer yielding data comparable to flow cytometry data," *Cytometry*, 12:381-387, 1991.
Kawamura et al., "DNA ploidy analysis of urinary tract epithelial tumors by laser scanning cytometry," *Anal. Quant. Cytol. Histol.*, 22(1):26-30, 2000.
Kessel et al., "Photodynamic therapy: a mitochondrial inducer of apoptosis," *Cell Death and Differentiation*, 6(1):28-35, 1999.
Leunig et al., "Angiogenesis, microvascular architecture, microhemodynamics, and interstitial fluid pressure during early growth of human adenocarcinoma LS174T in SCID mice," *Cancer Res.*, 52: 6553-6560, 1992.
Masunaga et al., "Sulindac Inhibits Growth of Rat Colon Carcinoma by Inducing Apoptosis," *Eur. Surg. Res.*, 32:305-309, 2000.
Matsuura et al., "Preoperative Treatment with Tegafur Suppositories Enhanced Apoptosis and Reduces the Intratumoral Microvessel Density of Human Colorectal Carcinoma," *Cancer*, 88:1007-1015, 2000.
Noodt et al., "Different apoptotic pathways are induced from various intracellular sites by tetraphenylporphyrins and light," *Brit. J. Cancer*, 79(1):72-81, 1999.
Oesterreich et al., "The small heat shock protein HSP27 is not an independent prognostic marker in axillary lymph node-negative breast cancer patients," *Clin. Cancer Res.*, 2:1199-1206, 1996.
Office Action issued by European Patent Office in European Application No. 01 992 888.6, mailed Dec. 27, 2007.
Office Action issued by IP Australia in Australian Application No. 2002217821, mailed Mar. 2, 2006.
Office Action issued by IP Australia in Australian Application No. 2002217821, mailed Nov. 6, 2007.
Office Action issued by United States Patent and Trademark Office in U.S. Appl. No. 10/145,275, mailed Jun. 28, 2005.
Office Action issued by United States Patent and Trademark Office in U.S. Appl. No. 10/145,275, mailed Oct. 11, 2005.
Office Action issued by United States Patent and Trademark Office in U.S. Appl. No. 10/145,275, mailed Mar. 31, 2006.
Office Action issued by United States Patent and Trademark Office in U.S. Appl. No. 10/145,275, mailed Oct. 31, 2006.
Office Communication issued by United States Patent and Trademark Office in U.S. Appl. No. 10/145,275, mailed Nov. 1, 2007.
Pasqualini et al., "Aminopeptidase N is a receptor for tumor-homing peptides and a target for inhibiting angiogenesis," *Cancer Res.*, 60:722-727, 2000.
Peng et al., "Distribution and photosensitizing efficiency of porphyrins induced by application of exogenous 5-aminolevulinic acid in mice bearing mammary carcinoma," *Int. J. Cancer*, 52:433-443, 1992.
Savill et al., "Phagocytic recognition of cells undergoing apoptosis," *Immunol. Today*, 14: 131-136., 1993.
Schlingemann et al., "Expression of the high molecular weight melanoma-associated antigen by pericytes during angiogenesis in tumors and in healing wounds," *Am J Pathol.*, 136: 1393-1405, 1990.
Schor et al., "Assessment or vascularity in histological sections: effects of methodology and value as an index of angiogenesis in breast tumors," *Histochemical J.*, 30:849-856, 1998.
Seifert et al., "Quantitation of angiogenesis in healing anastomoses of the rat colon" *Exp. Mol Pathol*, 64:31-40, 1997.
Shabisgh et al., "Early effects of castration on the vascular system of the rat ventral prostate gland" *Endocrinology*, 140:1920-1926, 1999.
Shaheen et al., "Antiangiogenic therapy targeting the tyrosin kinase receptor for vascular endothelial growth factor receptor inhibits the growth of colon cancer liver metastasis and induces tumor and endothelial cell apoptosis" *Cancer Research*, 59:5412-5416, 1999.
Tockmann et al., "Considerations in bringing a cancer biomarker to clinical application," *Cancer Res.*, 52:2711s-2718s, 1992.
Visscher et al., "Prognostic significance of image morphometric microvessel enumeration in breast carcinoma" *Anal. Quant. Cytol. Histol*, 15:88-92, 1993.
Vu et al., "MMP-9/gelatinase B is a key regulator of growth plate angiogenesis and apoptosis of hypertrophic chondrocytes," *Cell*, 93:411-422, 1998.
Weidner, "Intratumor microvessel density as a prognostic factor in cancer," *Amer. J. Path.*, 147:9-19, 1995.

\* cited by examiner

LSC Data Print Out
FIG. 2
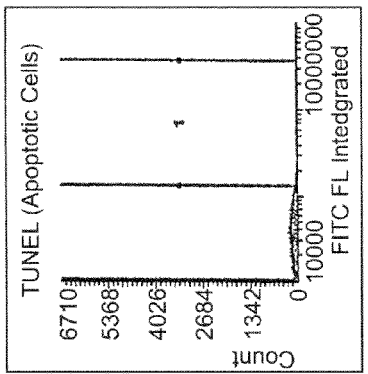
FIG. 2A
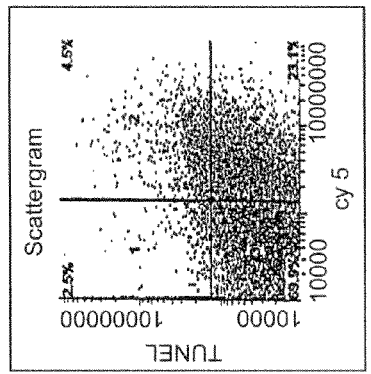
FIG. 2B
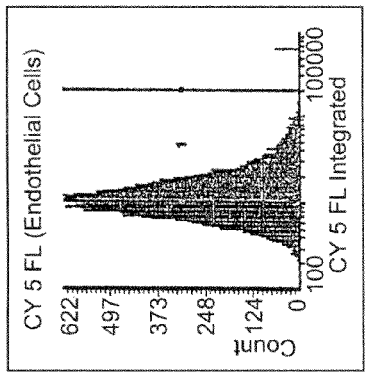
FIG. 2D
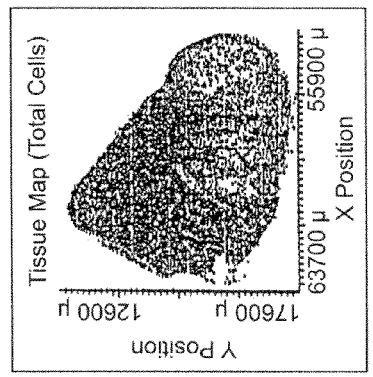
FIG. 2E
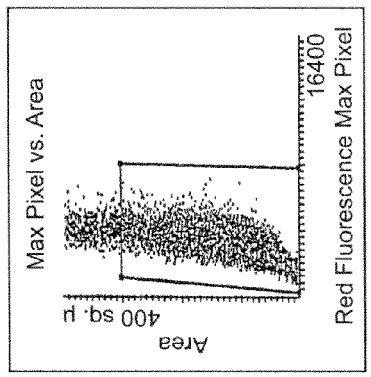
FIG. 2C
| cy5 Scattergram | | | | | | | |
|---|---|---|---|---|---|---|---|
| Rgn. # | Count | Pct. | Mean | FWHM | CV | Median | IQ rg | SD |
| 1 | 610 | 2.5% | -137066 | -71.8% | -261.3% | -37384 | -512.0% | 358200.4 |
| 2 | 1074 | 4.5% | 732253 | 24.9% | 99.4% | 478289 | 90.9% | 727868.2 |
| 3 | 16795 | 69.9% | -1613 | -3638.2% | -6656.7% | 15339 | 438.4% | 107424.6 |
| 4 | 5559 | 23.1% | 367910 | 15.8% | 108.8% | 247704 | 63.3% | 400440.0 |
| Total | 24038 | | 113193 | 64.9% | 229.6% | 47635 | 251.7% | 339113.3 |

LSC Data Print Out

LSC Data Print Out

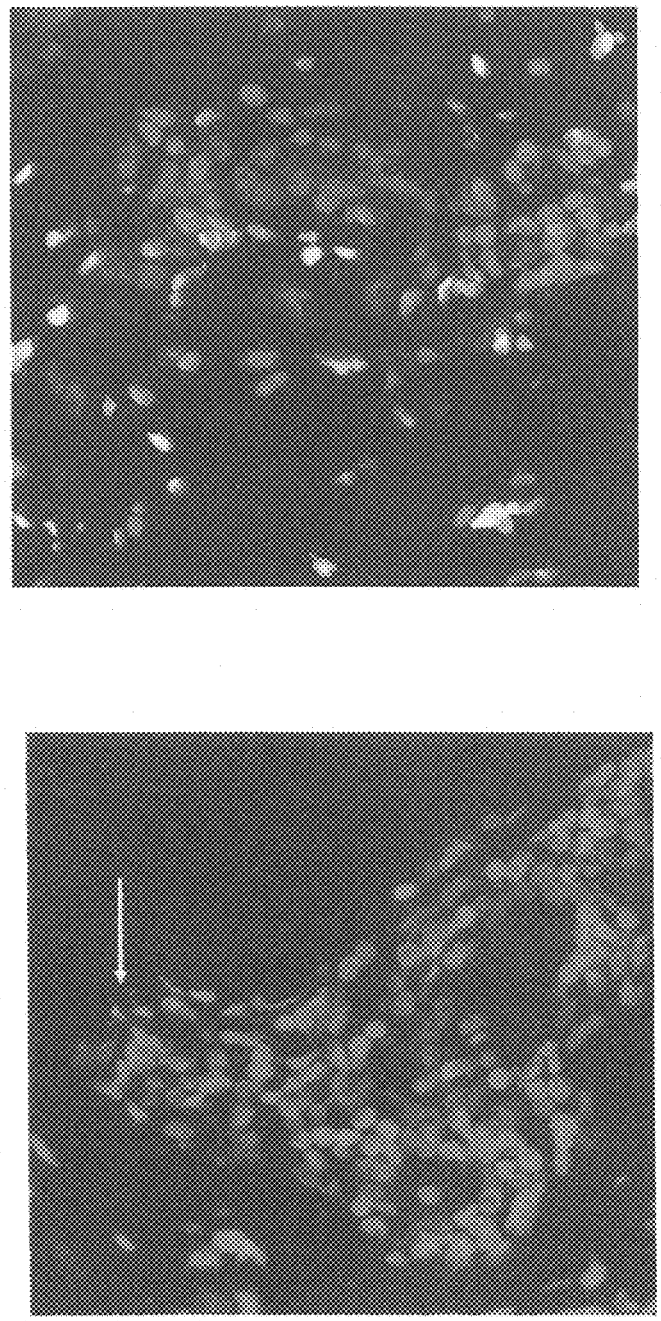
Figure 14 F — High Apoptosis in Patient With Complete Response (Pretreatment; 48 h After Chemotherapy)

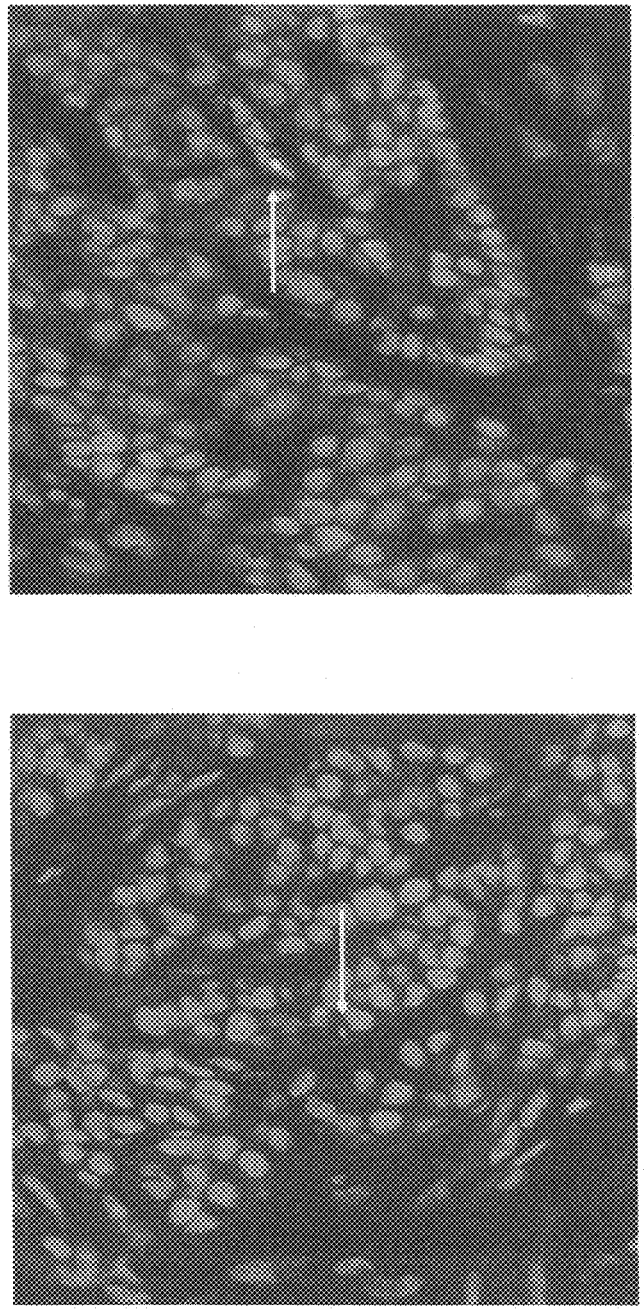
Figure 14 G. Low Apoptosis in Patient With Poor Response

Median points plotted to the left and right of B and F; EC Density decreased 1.3 fold post-treatment (56 days), p = 0.32.

LASER SCANNING CYTOMETRY MEDIATED ANALYSIS OF THERAPEUTIC EFFICACY IN TUMORS

This application is a continuation of U.S. Ser. No. 10/145,275, filed May 14, 2002 now abandoned, which was a continuation of PCT/US01/43806, filed Nov. 6, 2001, which in turn claims benefit of priority to U.S. Provisional Application Ser. No. 60/246,279 filed Nov. 6, 2000, the entire contents of each of the foregoing applications being incorporated by reference.

BACKGROUND OF THE INVENTION

I. Field of the Invention

The present invention relates generally to the field of cancer diagnosis and treatment, and more specifically relates to the use of laser scanning cytometry for the determination of endothelial cell death, endothelial tumor cell death and tumor blood vessel density. This method can be used as an indicator for therapeutic response and for determining treatment protocols.

II. Description of Related Art

Angiogenesis, or new blood vessel growth, has become a topic of major prominence in both the scientific literature and the popular press over the past several years. Public interest centers on scientific studies and clinical trials now underway that have demonstrated that inhibitors of angiogenesis can substantially reduce or even stop growth of solid tumors. This finding has lead to much interest and investment in angiogenesis research.

A new area for cancer treatment involves the use of anti-angiogenetic drugs, several of which are already in clinical trials. Angiogenesis is the process by which new blood vessels are formed. Although the exact mechanism of angiogenesis activation remains unknown, researchers have identified the existence of diffusable protein factors released by tumor cells that serve as angiogenesis-stimulators. Recent advances in cancer treatment are based on the fact that tumors, like other cells, require oxygen and other nutrients for growth and proliferation. Once the size of a tumor becomes greater than about 2 mm, a new supply of nutrients is needed for continued growth. Tumors may remain small and dormant state for an indefinite period of time. However, once tumors acquire the capacity induce angiogenesis and produce their own blood vessels, they may grow and metastasize to other regions of the body.

Anti-angiogenic therapy involves the inhibition of tumor growth by preventing the formation of new blood vessels. Scientific studies and clinical trials now underway that have demonstrated that inhibitors of angiogenesis can substantially reduce or even stop growth and metastasis of solid tumors. The major advantages of anti-angiogenic therapy is that these drugs, unlike chemotherapy, radiation therapy, and other traditional cancer treatments, have only mild side effects. The therapy does not cause the death of normal, healthy cells. Also, the body does not acquire resistance to treatment with anti-angiogenic compounds as it does with chemotherapeutic compounds.

Several methods for determining the efficacy of anti-angiogenic compounds exist and include the use of TUNEL (terminal deoxynucleotidyltransferase-uridine nick end labeling) and other labeling methods and a manual method for the determination of apoptosis in tumor cells. For example, see Dong et al. (1999), Ikeda et al. (1996), Shabisgh et al. (1999). Fluorescent dual-labeling of apoptotic endothelial cells has been shown by Shaheen et al., (1999). A method of determining the metastatic potential of a tumor by determining the presence of the pro-angiogenic factor VEGF transcripts is disclosed in U.S. Pat. No. 5,942,385.

Tumor vascularization also is used as a diagnostic tool for tumor growth and metastasis (Folkman et al., 1987). Determining vascularity of tumor tissue by immunohistochemical and non-invasive methods have been done by Fanelli et al. (1999), Griffey et al. (1998), Visscher et al. (1993), Seifert et al. (1997), and in U.S. Pat. No. 5,840,507. Other methods of determining vascular parameters include the use of magnetic resonance imaging (MRI) (U.S. Pat. No. 6,009,342) and the use of color doppler signals (Cosgrove et al., 1990). The use of computers to assist in the determination of vascular parameters has been demonstrated in U.S. Pat. Nos. 5,688,694 and 65,616,469 and by Fox et al., (1995) and has aided in the counting procedures. However, counting of microvessels in tumor samples, besides being labor-intensive, is a qualitative art. The method requires considerable technical training to obtain reliable and reproducible results, and inter-investigator variability is a significant problem. Difficulties in reproducing the method have been reported by several groups (Wiedner, 1995). Additionally, the process of preparing specimens for histology and counting vessels is time consuming. Therefore, the application of this technique has been limited generally to research purposes.

For the techniques described above, a waiting period after anti-cancer therapy is usually required before tumor vascularization can be determined. When using non-invasive methods of observing effects of cancer treatments, one must wait several weeks before changes in the tumor can be observed. This can cause problems, especially if practitioners need to know the efficacy of treatments that have substantial adverse side effects.

One concern that has arisen as anti-angiogenic therapies enter clinical trial is that anti-vascular agents may not be specific for the tumor vasculature. Because previous studies of angiogenesis have identified tumor blood vessels by staining them with antibodies to endothelial cell antigens (CD31, CD34), it has been difficult to directly evaluate potential toxicity to adjacent normal tissue.

A purpose of this invention is to determine whether apoptosis can be measured in tumor endothelial cells in situ and to use these methods to measure patient responses to anti-angiogenic and more traditional therapies; in other words, to confirm that the drug target has been hit and that the desired biological effects have been obtained.

Another purpose if this invention is to provide of method of determining anti-cancer therapeutic efficacy that can be used during or immediately after therapy.

While determination of apoptosis and vascular parameters of tissue are known in the art, A single method in which all of these parameters are determined is not available.

SUMMARY OF THE INVENTION

It is therefore an object of this invention to present a method for detection and diagnostic of viable tumor cells, tumor cell death, endothelial cell death, viable endothelial cells, endothelial cell density, and tumor blood vessel density of tumor tissue. It is also an object of this invention to determine apoptosis and blood vessel density without the need for laborious manual counting techniques.

Thus, the present invention contemplates a method for assessing anti-cancer therapeutic efficacy comprising (a) obtaining a tissue sample from a patient undergoing anti-cancer therapy or an animal used for anti-cancer therapy development; (9b) staining said sample with at least one fluorescent label; (c) subjecting the sample to laser scanning cytometry; and (d) obtaining data on the number of apoptotic endothelial cells, apoptotic endothelial tumor cells or blood vessel density (BVD) in the sample, wherein response to the treatment is determined by comparing said data to similar data from the tissue sample obtained either at a different time or at a different location than the first tissue sample. The response to the treatment may also be determined by comparing the data to similar data from tissue samples obtained prior to said anti-cancer therapy.

The response to the treatment is determined by comparing said data to a general standard, where a general standard of BVD is one obtained from averaging BVD values from tissue samples from multiple patients obtained from tumors at a known stage or at a known reduction in tumor size. The data obtained by this comparison can be represented in any form of a ratio.

The data obtained may comprise the number of apoptotic tumor endothelial cells, the number of apoptotic tumor cells in said sample and the blood vessel density in said sample. The data obtained may also comprise any two of these parameters. It is an aspect of this invention that the laser scanning cytometry is automated. It is an aspect of this invention that an automated analysis technique is used. The automated analysis technique comprises creating a tissue map and selectively gating said tissue map.

It is an aspect of this invention that staining comprises a double-fluorescence labeling technique which comprising a fluorescent marker of apoptosis such as dT-dUTP Nick End Labeling (TUNEL), fluorescently labeled caspace-3, propidium iodide, or sytox green and a fluorescent endothelial cell antibody such as an anti-CD31 or anti-CD34 antibody, an antibody labeled with Cy-5, or a secondary antibody conjugated to a fluorophore. The two or more labels are on the same tissue sample.

It is an aspect of this invention to subject the tissue sample to a laser scanning device, such as a CYTOMETER, which comprises contouring cell nuclei and contouring blood vessels. The contouring of cell nuclei and contouring of blood vessels occurs either simultaneously or sequentially.

It is an aspect of this invention that a sample is obtained prior to the anti-cancer therapy or during the anti-cancer therapy. It is also an aspect of this invention that the sample may be obtained after the anti-cancer therapy. The sample may be obtained less than 1, 2, 3, 4, 5, 6, 7, 8, 9, 10, 11, 12, 13, 14 or 15 hours after treatment. The sample also may be obtained less than 1, 2, 3, 4, 5, 6, 7, 8, 9, 10, 11, 12, 13, 14, 15, 20, or 25 days after treatment. The sample also may be obtained less than 1, 2, 3, 4, 5, 6, 7, 8, 9, 10, 11, 12, 24, 36, 48 or 60 months after treatment. It is also contemplated that the sample may be obtained 10, 15, 20, 30, or 40 years after treatment. It is further contemplated that 1, 2, 3, 4, 5, 6, 7, 8, 9, 10, 15, 20, 25, 30, 35, 40, 45, 50 or more tissue samples are obtained.

Another aspect of this invention is that the anti-cancer therapy comprises the use of an anti-angiogenic agent. The angiogenic agent may be, but is not limited to angiostatin, endostatin, an inhibitor of the receptor for endothelial growth factor, or a vascular endothelial growth factor (VEGF) receptor tyrosine kinase inhibitor. An example of an inhibitor that blocks receptor for endothelial growth factor is C225. VEGF receptor tyrosine kinase inhibitors are small, synthetic, selective molecules, examples of which are SU5416, a selective inhibitor of the VEGF receptor, and SU6668, an inhibitor of the receptors for VEGF, bFGF, and PDGF. SU5416 and SU6668 can be obtained from SUGEN, Inc. (Shaheen et al. 1999).

It is an aspect of this invention that said anti-cancer therapy comprises the use of angiogenic, chemotherapeutic or radiotherapeutic agent. The patient may have a cancer selected from the group comprising of head and neck, brain, lung, liver, spleen, kidney, lymph node, small intestine, pancreas, blood cells, colon, stomach, breast, cervix, bladder, endometrium, prostate, testicle, ovary, skin, esophagus, bone marrow and blood cancer.

Another aspect of the invention comprises a kit comprising a fluorescent label for endothelial cell markers such as antibodies for CD31 or CD34, a fluorescent label for cell nuclei such as dUTP-FITC, TAQ polymerase and buffer for use in assessing anti-cancer therapeutic efficacy with laser scanning cytometry. The kit may also comprise antigen retrieval buffer for paraffin sections.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIGS. 2 A-E—LSC scan of an untreated mouse tumor. FIG. 2A shows total cells contoured. FIG. 2B shows endothelial cell fluorescence using CY 5. FIG. 2C shows TUNEL positive cell fluorescence using FITC. FIG. 2D is a 'tissue map' created following the completion of the scan. FIG. 2E contains four quadrants and provide the number of apoptotic tumor cells (quadrant 1) and apoptotic endothelial cells (quadrant 2). The gating set in FIG. 2E is based on fluorescent positive cells which can be found in FIG. 2B for endothelial cells and in FIG. 2C for TUNEL positive cells.

FIG. 3A shows the total cells contoured. FIG. 3B shows endothelial cell fluorescence using CY 5. FIG. 3C shows TUNEL positive cell fluorescence using FITC. FIG. 3D is a 'tissue map' created following the completion of the scan. FIG. 3E contains four quadrants and provide the number of apoptotic tumor cells (quadrant 1) and apoptotic endothelial cells (quadrant 2). The gating set in FIG. 3E is based on fluorescent positive cells which can be found in FIG. 3B for endothelial cells and in FIG. 3C for TUNEL positive cells.

FIG. 14F—Representative image of tumor cell apoptosis in a human breast tumor biopsy pre- and post-chemotherapy (48 hrs.) before it is scanned by the LSC. This patient had a complete clinical response. FIG. 14G—Representative image of tumor cell apoptosis in a human breast tumor biopsy pre- and post-chemotherapy (48 hrs.) before it is scanned by the LSC. This patient had no clinical response. FIG. 14H—Bar graph showing the percent change in apoptotic tumor cells post-chemotherapy (24 & 48 hrs.). The patients that had a complete clinical response demonstrated significant changes in tumor cell apoptosis compared to baseline levels. The patients that did not respond to the chemotherapy (no clinical response) demonstrated lower levels of apoptosis that were not significant compared to baseline.

FIG. 15A shows tumor cell death data, with a difference of 0.23 observed. FIG. 15B shows change in tumor endothelial cell death. FIG. 15C shows change in blood vessel density.

FIG. 17B Graph showing that Endostatin decreased ED 1.3 fold following 56 days of treatment.

DESCRIPTION OF ILLUSTRATIVE EMBODIMENTS

I. The Present Invention

Figure 1:
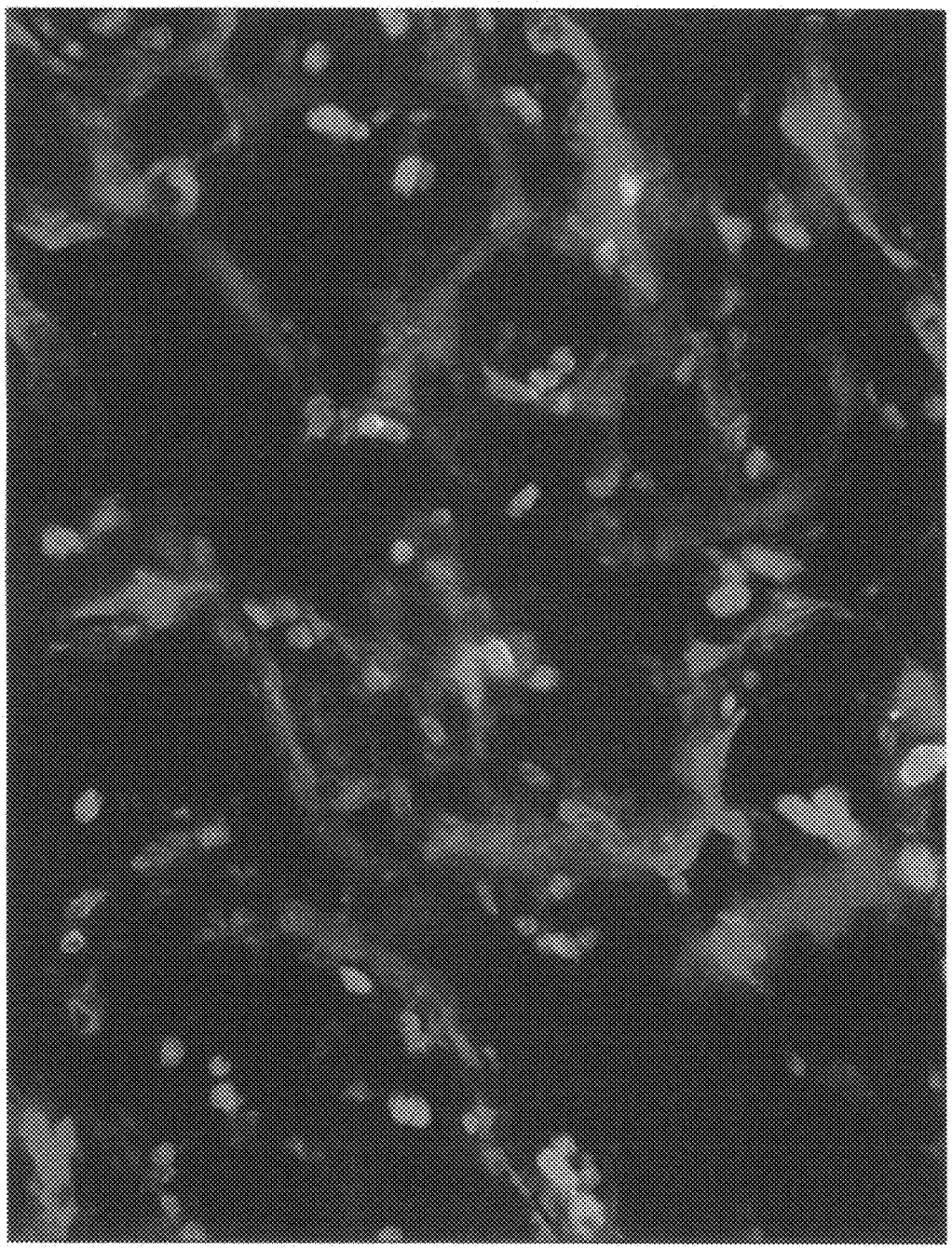
FIG. 1—Representative image of a stained pre-clinical tumor tissue sample, captured using a fluorescent microscope. Endothelial cells (CD31) are stained red and apoptotic cells (TUNEL) appear green and yellow.

This invention describes the use of laser scanning cytometry (LSC) to determine endothelial cell death, endothelial tumor cell death and tumor blood vessel density of tumor tissue. These parameters are sensitive markers of efficacy in tumors treated with anti-angiogenic and more traditional therapies and can be used to distinguish the anti-cancer therapeutic efficacy of the treatment. The present invention overcomes deficiencies in the art by combining the determination of these three parameters into a single automated method. Also, the present invention is the earliest diagnostic assay available.

Anti-cancer therapeutic efficacy is determined by the increase in the health of the patient. An anti-cancer agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the life-span of a subject with a cancer. Anti-cancer agents include, for example, angiogenic agents, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

II. Angiogenesis

One of the processes involved in the growth of both primary and secondary (metastatic) tumors is neovascularization, or creation of new blood vessels which grow into the tumor. This neovascularization is termed angiogenesis (Folkman, 1986; Folkman, 1989), which provides the growing tumor with a blood supply and essential nutrients. Although tumors of 1-2 mm in diameter can receive all nutrients by diffusion, further growth depends on the development of an adequate blood supply through angiogenesis. Inhibition of angiogenesis provides a novel and more general approach for treating both primary and secondary tumors by manipulation of the host microenvironment.

The induction of angiogenesis is mediated by several angiogenic molecules released by tumor cells, tumor associated endothelial cells and the normal cells surrounding the tumor endothelial cells. The prevascular stage of a tumor is associated with local benign tumors, whereas the vascular stage is associated with tumors capable of metastasizing. Moreover, studies using light microscopy and immunohistochemistry concluded that the number and density of microvessels in different human cancers directly correlate with their potential to invade and produce metastasis (Weidner et al., 1991; 1993). Not all angiogenic tumors produce metastasis, but the inhibition of angiogenesis prevents the growth of tumor endothelial cells at both the primary and secondary sites and thus can prevent the emergence of metastases.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent and unregulated angiogenesis is characteristic of tumor growth and it supports the pathological damage seen in these cancer. Thus, tumor growth is an angiogenesis-dependent process (Folkman, 1971). After an initial prevascular phase, every increase in tumor endothelial cell population is preceded by an increase in new capillaries converging on the tumor. Expansion of tumor volume beyond this phase requires the induction of new capillary blood vessels.

More than 50 compounds that interfere with angiogenesis in laboratory animals and/or interfere with growth of endothelial cells in cell cultures have been identified. Some anti-angiogenesis drugs that are currently under development or that have already been tested include: SU5416, SU6668, C225, AG3340, AGM 1470 (or TNP 470), Angiostatin, Anti-ED-B Mab, Anti-VEGI, Antisense phosphorothionate oligonucleotides, B-0829, Batimastat, BAY 12-9566, BB 2516 (or Marimastat), CAI (or Carboxyamidotriazole), CI 994, CM 101, COL-3, Combrestatin A4 Phosphate, CT-2584, Dimethylxanthenone acetic acid, Dalteparin, Endostatin, FCE 26644 and FCE 26950, FR-111142, Genistein, GM 1474, Interleukin-12 (IL-12), IM-862, Integrin alphavbeta3, Linimide, Marimastat (or Batimastat), Metastat, OLX-514, Penicillamine, Platelet Factor 4, Polysulfated polysaccharide from seaweed cell walls, Soluble FLT-1 VEGF Receptor, SPARC, Squalamine lactate, Suramin, SU-101, SU-5416, Tecogalan, Thalidomide, Thrombosporin, VEGF Inhibitor and Vitaxin. Other agents shown to have anti-angiogenic behavior in reported pre-clinical tests include 2-Methoxyestradiol, Doxy, Monoclonal Antibody, Shark Cartilage, Angiogenin, Fish Oil, Neovastat, Spironolactone, Basal Lamina, Flavone Acetic Acid, Nigella Sativa, Squalamine, Captopril, Hormonal Deprivation, P53 Gene Therapy, Thunder God Vine, CM101, Human Tumor Inhibitors, Pentosan Polysulfate, Tie2 Pathway, Combretastatin, Interleukin-1 Receptor Antagonist, Peptide Delivery System, TIMP-1, Contortrostatin, Interleukin-8, PI-88, TNF, COX-2, Irsogladine, PSK, Troponin, Curcumin, Kringle 5 of Plasminogen, Retinoids, Vinblastine, Diphenylureas, Mitoxantrone, Scatter Factor and Vitamin E. (http://www.slip.net/~mcdavis/-miscangi.html).

Some chemotherapy drugs have also been found to have some anti-angiogenic effects, for example paclitaxel (Taxol), doxorubicin (Adriamycin), epirubicin, mitoxantrone and cyclophosphamide. However, because these drugs kill some normal cells as well as cancer cells, they must be given in cycles. Anti-angiogenic drugs are usually given without interruption. Chemotherapy drugs are not considered pure anti-angiogenic drugs, and are generally used for their ability to destroy tumor cells in a different stage of a cell's life cycle. Since chemotherapy drugs tend to have severe side effects, the ability to monitor the efficacy of these drugs early in the treatment process would be advantageous.

Work conducted over the past decade has clearly demonstrated that tumor angiogenesis is rate-limiting for the growth of solid tumors, making vascular targeting an attractive strategy for therapeutic intervention. Angiogenesis in normal tissues and tumors is controlled by a balance between pro- and anti-angiogenic molecules. Previous work has shown that proangiogenic factors such as vascular endothelial growth factor (VEGF) and basic fibroblast growth factor (bFGF, or FGF-2) have pleiotropic effects on endothelial cells, including promotion of growth, invasion, and differentiation. However, more recent studies suggest that certain endothelial cells are also dependent on them for survival. For example, incubating human umbilical vein endothelial cells (HUVECs) in serum-free medium stimulates apoptosis, and this response can be attenuated by addition of bFGF to the culture medium (Karsan et al., 1997). Similarly, other work has shown that VEGF can also inhibit apoptosis induced by serum withdrawal (Gerber et al., 1998; Nor et al., 1999 as well as death induced by cellular detachment (aniokis) (Watanabe et al., 1997) or exposure to tumor necrosis factor (Spyridopoulos et al., 1997). Active investigation has identified candidate mechanisms for these effects. Basic FGF and VEGF each has been reported to stimulate increased expression of the anti-apoptotic protein, BCL-2, in endothelial cells in vitro (Karsan et al., 1997; Gerber et al., 1998; Nor, 1999), and VEGF can also apparently upregulate expression of two inhibitors of apoptosis (IAP's), survivin and XIAP, in HUVEC cells (Tran et al., 1999). Upstream of BCL-2, one group has reported that VEGF-mediated survival requires MAP kinase activation and parallel downregulation of Jun kinase (Gupta et al., 1999). Another group has demonstrated crosstalk between VEGF and integrin signaling leading to activation of the cell survival-associated protein serine/threonine kinase, AKT/PKB (Fufio et al., 1999).

Other recent studies have identified factors that negatively regulate angiogenesis, and where interrogated, these molecules appear to promote apoptosis in endothelial cells. Angiostatin, which is an internal cleavage product of plasminogen, was purified from culture supernatants of the Lewis lung adenocarcinoma via its ability to inhibit angiogenesis in in vitro assays. The first suggestion that it would act by inducing apoptosis came from tissue kinetic studies in xenograft tumors, where angiostatin had no effect on rates of endothelial cell proliferation but increased the relative proportion of tumor cells undergoing apoptosis (O'Reilly et al., 1996).

Subsequent studies revealed that angiostatin can directly induce apoptosis in endothelial cells (Claesson-Welsh et al., 1998), although the biochemical mechanisms involved remain unclear. Very similar data are available for endostatin, a polypeptide fragment derived from collagen XVIII (O'Reilly et al., 1997). Like angiostatin, endostatin promotes tumor dormancy in vivo (O'Reilly et al., 1997) and endothelial cell apoptosis in vitro (Dhanabal et al., 1999). Importantly, systemic administration of angiostatin or endostatin can promote the regression of established human tumors and overall survival in nude mice (O'Reilly et al., 1996; O'Reilly et al., 1997), and repeated administration does not appear to induce drug resistance (Boehm et al., 1997). In addition, other studies indicate that specific angiogenesis inhibitors may act at different stages of tumor progression (Bergers et al., 1999), suggesting that a single anti-angiogenic agent might not be effective in all solid tumors. It would be extremely beneficial to determine anti-cancer therapeutic efficacy and design patient-tailored therapies that are able to predict whether or not endothelial cell apoptosis will occur in response to vascular targeting in a particular patient's tumor.

III. Traditional Cancer Therapies

The use of the current invention to determine anti-cancer therapeutic efficacy of more traditional cancer therapies is contemplated. The determination of endothelial cell death, endothelial tumor cell death and tumor blood vessel density of tumor tissue can aid in the determination of therapy effectiveness for the therapies in which the mechanisms involve similar mechanisms. The ability to measure the efficacy of traditional cancer therapies with the method of the current invention is advantageous in that, instead of waiting for up to three months for a positive effect, the practitioner can see if the therapies is working much sooner, and can limit the toxicity to the patient if the therapy is not working.

A. Chemotherapeutic Agents

The term "chemotherapy" refers to the use of drugs to treat cancer. A "chemotherapeutic agent" is used to connote a compound or composition that is administered in the treatment of cancer. One subtype of chemotherapy known as biochemotherapy involves the combination of a chemotherapy with a biological therapy.

Chemotherapeutic agents include, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP 16), farnesyl-protein transferase inhibitors, gemcitabine, ifosfamide, mechlorethamine, melphalan, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, corticosteroid hormones, mitotic inhibitors, and nitrosoureas, hormone agents, miscellaneous agents, and any analog or derivative variant thereof.

Chemotherapeutic agents and methods of administration, dosages, etc. are well known to those of skill in the art (see for example, the "Physicians Desk Reference", Goodman & Gilman's "The Pharmacological Basis of Therapeutics" and in "Remington's Pharmaceutical Sciences", incorporated herein by reference in relevant parts), and may be combined.

Some chemotherapeutic agents for which the determination of efficacy is contemplated in this invention are alkylating agents such as a nitrogen mustard (chlorambucil (also known as leukeran), cyclophosphamide, melphalan), an ethylenimene and/or a methylmelamine, an alkyl sulfonate, nitrosureas, (carmustine or sterile carmustine, lomustine), a triazine, an antimetabolite (folic acid analogs, pyrimidine analogs, purine analogs), natural products (mitotic inhibitors such as epipodophyllotoxins, taxoids and vinca alkaloids), antitumor antibiotics (doxorubicin hydrochloride, daunorubicin hydrochloride, mitomycin, actinomycin D, bleomycin), hormonal therapy (corticosteroid hormones, hydroxyprogesterone caproate, medroxyprogesterone acetate, and megestrol acetate), platinum coordination complexes, anthracenedione, a substituted urea, a methyl hydrazine derivative, an adrenocortical suppressant and aminoglutethimide.

B. Radiotherapeutic Agents

Radiotherapeutic agents include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these agents effect a broad range of damage DNA, on the precursors of DNA, the replication and repair of DNA, and the assembly and maintenance of chromosomes.

Radiotherapeutic agents and methods of administration, dosages, etc. are well known to those of skill in the art, and may be combined with the invention in light of the disclosures herein. For example, dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapeutic Agents

An immunotherapeutic agent generally relies on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (e.g., a chemotherapeutic, a radionuclide, a ricin A chain, a cholera toxin, a pertussis toxin, etc.) and serve merely as a targeting agent. Such antibody conjugates are called immunotoxins, and are well known in the art (see U.S. Pat. Nos. 5,686,072, 5,578,706, 4,792,447, 5,045,451, 4,664,911, and 5,767,072, each incorporated herein by reference). Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

a. Immune Stimulators

In a specific aspect of immunotherapy is to use an immune stimulating molecule as an agent, or more preferably in conjunction with another agent, such as for example, a cytokines such as for example IL-2, IL-4, IL-12, GM-CSF, tumor necrosis factor; interferons alpha, beta, and gamma; F42K and other cytokine analogs; a chemokine such as for example MIP-1, MIP-1 beta, MCP-1, RANTES, IL-8; or a growth factor such as for example FLT3 ligand.

One particular cytokine contemplated for use in the present invention is tumor necrosis factor. Tumor necrosis factor (TNF; Cachectin) is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anti-cancer activity.

Another cytokine specifically contemplate is interferon alpha. Interferon alpha has been used in treatment of hairy cell leukemia, Kaposi's sarcoma, melanoma, carcinoid, renal cell cancer, ovary cancer, bladder cancer, non-Hodgkin's lymphomas, mycosis fungoides, multiple myeloma, and chronic granulocytic leukemia.

b. Passive Immunotherapy

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. However, their application is somewhat limited by their scarcity and have so far only been administered intralesionally. For example, human monoclonal antibodies to ganglioside antigens have been administered intralesionally to patients suffering from cutaneous recurrent melanoma (Irie & Morton, 1986). Regression was observed in six out of ten patients, following, daily or weekly, intralesional injections. In another study, moderate success was achieved from intralesional injections of two human monoclonal antibodies (Irie et al., 1989). It may be favorable to administer more than one monoclonal antibody directed against two different antigens or even antibodies with multiple antigen specificity. Treatment protocols also may include administration of lymphokines or other immune enhancers (Bajorin et al. 1988).

c. Active Immunotherapy

In active immunotherapy, an antigenic peptide, polypeptide or protein, or an autologous or allogeneic tumor cell composition or "vaccine" is administered, generally with a distinct bacterial adjuvant (Ravindranath & Morton, 1991; Morton & Ravindranath, 1996; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be antiganglioside or anticarbohydrate antibodies.

d. Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated anigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond.

D. Genetic Therapy Agents

A tumor cell resistance to agents, such as chemotherapeutic and radiotherapeutic agents, represents a major problem in clinical oncology. One goal of current cancer research is to find ways to improve the efficacy of one or more anti-cancer agents by combining such an agent with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that the efficacy of gene therapy could be determined by using the method of this invention.

a. Inducers of Cellular Proliferation

In one embodiment of the present invention, it is contemplated that anti-sense mRNA directed to a particular inducer of cellular proliferation is used to prevent expression of the inducer of cellular proliferation. The proteins that induce cellular proliferation further fall into various categories dependent on function. The commonality of all of these proteins is their ability to regulate cellular proliferation.

For example, a form of PDGF, the sis oncogene, is a secreted growth factor. Oncogenes rarely arise from genes encoding growth factors, and at the present, sis is the only known naturally-occurring oncogenic growth factor.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

Other proteins such as Jun, Fos and Myc are proteins that directly exert their effects on nuclear functions as transcription factors.

b. Inhibitors of Cellular Proliferation

In certain embodiment, the restoration of the activity of an inhibitor of cellular proliferation through a genetic construct is contemplated. Tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the G. The activity of this enzyme may be to phosphorylate Rb at late $G_1$. The activity of CDK4 is controlled by an activating subunit, D-type cyclin, and by an inhibitory subunit, the p16$^{INK4}$ has been biochemically characterized as a protein that specifically binds to and inhibits CDK4, and thus may regulate Rb phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

16$^{INK4}$ belongs to a newly described class of CDK-inhibitory proteins that also includes p16$^B$, p19, p21$^{WAF1}$ and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type p16$^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zacl, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

c. Regulators of Programmed Cell Death

In certain embodiments, it is contemplated that genetic constructs that stimulate apoptosis will be used to promote the death of diseased or undesired tissue. Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., Bcl$_{xL}$, Bcl$_w$, Bcl$_s$, Mcl-1, Al, Bfl-1) or counteract Bcl-2 function and promote cell death (e.g., Bax, Bak, Bik, Bim, Bid, Bad, Harakiri).

E. Other Biological Agents

It is contemplated that agents listed above may be used in combination to improve the therapeutic efficacy of treatment. The efficacy can then be measured with the method of this invention. Additional agents that may be used include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

IV. Endothelial Cell Death

The process of apoptosis was originally defined on the basis of a series of stereotyped morphological alterations that were observed in whole tissues (Kerr et al., 1972). Indeed, morphological identification of apoptotic cells in tumors has been used successfully in tumor xenograft studies to measure the effects of radiation therapy (Stephens et al., 1991). However, quantification is tedious, and the rapid removal of cells in the late stages of apoptosis by tissue macrophages and adjacent cells (Savill et al., 1993) probably results in underestimation of the actual number of affected cells when this technique is used. More recently, biochemical markers of apoptosis identified in vitro (DNA fragmentation, caspase activation, and surface phosphatidylserine exposure) have been used successfully to specifically image apoptosis in tissues in situ (Savill et al., 1993; Grasl-Kraupp et al., 1995). Of these endpoints, most studies have employed the TUNEL technique to quantify the specific 5'-OH double-strand DNA breaks that occur during the response (Savill et al., 1993). Although false-positive results obtained with the TUNEL technique have been reported (Grasl-Kraupp et al., 1995), the method has proven to be a very reliable alternative to the morphology-based assays and does not require extensive experience with the diverse morphological characteristics of apoptotic cells. However, most of the results obtained on endothelial cell death is from pre-clinical trials. Data from human patients on endothelial cell apoptosis has not been available before now.

Although tumor endothelial cells can be identified by standard CD31/34 staining, the ability to detect heterogeneity within the tumor vasculature offers distinct advantages to our efforts to study the death of endothelial cells. Specific detection of tumor endothelial cells within affected tissues that also contain normal cells will allow for parallel measurements of cell death in the tumor and normal compartments of affected tissues, thereby producing a direct measure of the potential toxicity of traditional and novel agents to normal vasculature. Most importantly, it is possible that further characterization of tumor endothelial heterogeneity will reveal subpopulations of cells that are dependent on particular vascular growth factors for their survival (Bergers et al., 1999), and patient therapy can be tailored to target these pathways and optimize clinical response.

V. Vascularity and Blood Vessel Density

Recent advances in in vivo imaging have allowed for the first direct comparisons of the functional properties of tumor and normal vasculature (Leunig et al., 1992). These studies indicate that intratumoral interstitial pressure is substantially elevated compared to adjacent normal tissue, and subsequent work has shown that tumor blood flow properties differ substantially from those observed in normal tissues (Gazit et al., 1997). Other work has shown that angiogenic blood vessels are phenotypically distinct from the normal vasculature with respect to expression of a variety of surface markers, including particular integrins ($\alpha_v\beta133$) (Friedlander et al., 1995), matrix metalloproteases (Vu et al., 1998), and high molecular weight proteoglycan (Schlingemann et al., 1990). These observations have led to the hypothesis that the distinct properties of tumor blood vessels might serve as targets for therapeutic intervention.

Phage display has been used successfully in vitro to identify receptor ligands and other partners in protein-protein interactions. Recently this strategy was used successfully to identify peptide motifs capable of tissue-specific binding in vivo (Pasqualini et al., 1996). Subsequent characterization of the peptide targets revealed that they were expressed on tissue endothelial cells, thereby establishing that tissue-specific blood vessel phenotypes can be identified (Rajotte et al., 1998). Extending these studies, the investigators were able to use an identical strategy in tumor-bearing mice to identify peptides that bind selectively to the tumor vasculature. These peptides do not interact with normal vascular endothelial cells, and they can be used to specifically direct anti-cancer therapies to tumors in vivo (Arap et al., 1998). The receptor for one of these peptides (NGR) has recently been identified as aminopeptidase N (CD13), and functional analyses confirm that CD13 expression is enhanced in endothelial cells within mouse and human tumors (Pasqualini et al., 2000).

The growth of microvessels differs in carcinomas. However, the exquisite localization of capillaries at the interface of glands and stroma which characterizes benign tissues is not present in carcinoma. In carcinoma, there is an increase in the number of capillaries with no apparent orientation with respect to malignant glands and cells. Therefore, carcinomas characteristically have an increased number of capillaries with a fairly uniform distribution as opposed to benign growths which contain an asymmetric orientation around glandular acini.

Pasqualini and Arap have obtained strong evidence that tumor endothelial cells express specific surface antigens that are not expressed by normal endothelial cells. For example, they have identified that aminopeptidase N (CD13) is a selective marker of tumor vasculature (Pasqualini et al., 2000) and that it can be used to direct therapy selectively to the tumor endothelium (Arap et al., 1998).

A variety of methods may be utilized to quantitate vascularity, including both indirect methods which measure factors associated with vascular components or blood vessel growth, and direct methods which directly quantitate blood vessels through manual or computer-aided morphometry. Indirect methods for determining vascularity measure factors associated with vascular components or blood vessel growth and may utilize ascitic fluids, or extracts of tissue samples obtained by a variety of methods, including for example, aspiration needle biopsy, needle biopsy or resection. A wide variety of factors may be quantitated in such samples, including for example proteins, carbohydrates, or other factors which are associated with vascular components or blood vessel growth. Representative examples include fibrin or fibrinogen (Svanberg, 1975), as well as many "angiogenic factors" which are associated with blood vessel growth (e.g., angiogenic heparin-binding endothelial cell growth factors, angiogenin, transforming growth factors, and other angiogenic factors) (Folkman et al., 1987). Techniques include Doppler sonography, dynamic contrast-enhanced MRI and PET scans have also been used (Fanelli et al. 1999; Griffey et al. 1998; Fox et al., 1995; Visscher et al., 1993, U.S. Pat. No. 5,688, 694). The current standard for determining vascularity is a histological assay.

One aspect of this invention includes the use of LSC to image blood vessels within a tissue sample. The use of LSC with computer-assisted calculations has not been used to determine vascular parameters of tumor and surrounding tissues. An advantage of using LSC for detecting vascular parameters is that, when the total number of cells within a tissue are known, a density calculation relative to the number of cells in the given tissue can be made as opposed to a calculation of the number of blood vessels relative to the area of the given tissue on a coverslip.

Blood vessel density is defined herein as the number of blood vessels as determined from analyzing the fluorescence emission of markers bound to the endothelial cells divided by the total number of cells in the tumor as determined from analyzing the fluorescence emission of markers bound to the cell nuclei. Endothelial cell density is measured because it is a more sensitive marker. Breaks in fluorescence of the endothelial cell stain will delimitate individual blood vessels.

VI. Laser Scanning Cytometry

To date, most investigators have used conventional (colorimetric) development strategies to identify TUNEL-positive cells in situ. A clear advantage of colorimetric methods is that they allow for direct, simultaneous visualization of DNA fragmentation and tumor morphology. However, signal-to-background differences can be slight, especially given that basal rates of cell death can be very low (under 2%). Furthermore, identifying dying tumor stromal and endothelial cells against the high background of tumor epithelial cells has been extremely difficult, and accurately quantifying them practically impossible.

One serious drawback with immunohistochemical analysis of tumor tissue is that relevant biological parameters must be measured manually, usually by counting positive cells in a number of high power microscope fields. While this does allow the investigator to exclude areas of the tumor that are not relevant (i.e., necrotic areas), data acquisition is time-consuming, and inter-investigator variability is a significant problem.

Fluorescence-based antigen detection systems offer several advantages over standard colorimetric strategies for antigen analysis in tissues. In general, fluorescent staining generates much higher sensitivity (signal-to-background), and it allows for more complex analyses of subcellular antigen distribution to be performed (by confocal microscopy). Substantial improvements in image analysis hardware and software have made quantification of fluorescent signals extremely straight-forward, and tissue can be stained simultaneously with multiple probes that have non-overlapping fluorescent properties. Laser scanning cytometry (LSC) is a combination of the flow cytometric techniques of fluorochromatic cell sample excitation and microscopic analysis with sample presentation (see Kamentsky et al., 1990; Kamentsky et al., 1991). A laser beam scans a sample on a fixed medium such as a slide, and the position of the cells and each cell figures are simultaneously determined and recorded. The ability of LSC to visualize cells is a distinct advantage. An additional advantage is that a greater amount of data can be obtained than from a standard flow CYTOMETER or a immunohistochemical count. Features such as area, perimeter, maximum pixel value and texture can all give additional information useful in characterizing differences within the staining patterns of the sample tissue. Details regarding LSC methods are known in the art. See Clatch et al. (1998); U.S. Pat. Nos. 5,427,910; 5,793,969; 5,885,840; and Kawamura et al. (2000), each of which are herein incorporated by reference.

The LSC instrument is more accurate than many other analysis techniques because it is capable of analyzing a large quantity of intact cells (both nucleus and cytoplasm) and subsequently renders greater accuracy in testing based on statistical sampling. This is due to the ability of LSC software to routinely analyze many cells/slide, as compared to image analysis, which analyzes typically 50-100 cells/slide. LSC is used to routinely measure more than 50,000 cells/slide and can be used to measure upwards of $10^7$ cells/slide. Conversely, LSC is also able to measure samples in which only a small number of cells are available. Fluorescence activated cell sorter (FACS) -based methods require a minimum of 10,000 cells in order to obtain data while LSC can give valid data with fewer than 100 cells. The quantitative ability of LSC makes it an ideal tool for obtaining more exact quantitative measurements of tumor cell properties. It is demonstrated herein that LSC can be used to obtain exact quantitative measurements of tumor EC apoptosis, tumor cell apoptosis, and viable tumor cell (FIGS. 2E and 3E).

The LSC methods described herein also permit improved specificity because the LSC methodology allows application of multiple marker agents, which facilitates enhanced specificity in testing. With fluorescent probes having narrow emission spectra and several excitation sources, it is possible to use 1, 2, 3, 4, 5, 6, 7 or more different marker agents. Furthermore, the LSC methodology includes production of a histogram which provides valuable information in helping to differentiate carcinoma from atypical cells (e.g., virally-infected cells). It is contemplated that the LSC will be used to measure light scattering as well as fluorescence of the sample tissue.

The LSC automatically measures fluorescence at multiple wavelengths of cells that have been treated with one or more fluorescent dyes in order to rapidly assay multiple cellular constituents by contouring the cell nuclei and blood vessels. Sequential scans of the same sample can be obtained and co-added, with the position of the individual cells recorded by the software. The laser optical train is designed to produce a large depth of field with nearly collimated excitation to achieve accurate constituent measurements independent of cell position in the slide focus. The spot size of the laser beam is preferably similar to the sample size. If photomultipliers are used, band pass filters can be added to isolate the fluorescence emission incident on each of the photomultiplier tubes.

Any intense light source that excites the fluorescence of the sample can be used. Preferred excitation sources include argon ion and He-Ne lasers. Visible, UV and near-IR light can be used, with visible light being preferred. In one aspect of the invention, contouring of the cell nuclei and contouring of the blood vessels is done simultaneously, using more than one laser incident on the sample at the same time. This requires modification of the current LSC system. However, the use of multiple excitation sources incident on a single sample is known in the art. It is conceived that there will be 2, 3, or 4 laser beams simultaneously incident on the sample for detection of multiple fluorescent markers. The advantages of this aspect of the invention includes a reduction in the time required to collect the data because it will not be necessary to switch between excitation sources after each scan.

The detector for the LSC can be either photomultiplier tubes, a CCD camera, or several CCD cameras. Filters, both physical and virtual can be used to reduce noise in the system. Cellular noise such as nuclear debris or overlapping nuclei can be gated out by special statistical filters.

Cells are measured and retained on a solid support. In a specific embodiment the solid support is a slide, and the slide position and laser beam are moved under computer control. Since the position of the slide and laser beam is known to the computer, cell position on the slide is a measurement feature. Interactions of each cell and the laser beam are measured and recorded many times in a two-dimensional array and features computed from these interactions are derived.

The software for LSC allows for the detection of multiple geographic regions for automatic scanning of a sample. The data obtained from the analysis are collected and stored within a computer file. Values for different fluorescence channels (for example, green, orange and long red) are obtained. A scattergram of y position versus x position maps the location of the cells on a slide.

Contemplated in this invention is the addition of a video screen to the LSC. The fluorescence image obtain from the LSC software could be imaged on video screen including a cursor or other pointer with which to select the area of the sample to analyze. This would give a simple method for the user to obtain data on only the relevant part of a tissue sample.

VII. Cell Samples

Obtaining a tissue sample can be achieved by any one of a variety of different means, largely depending on the nature of the sample to examined. For example, for examination of solid tissues, samples can be taken by biopsy which can be obtained through needle biopsy, endocscopy, laproscopy, or systoscopy. Alternatively, scrapings of cells can be taken from the tissue of interest. In an embodiment, the sample to be analyzed contains primarily tumor epithelial cells.

Once obtained, it may be necessary to further process the samples before they are examined. Further processing may include various forms of physical arrangement of the samples. For example, with solid tissues, it may be necessary to prepare thin sections. It also may be desired to dissociate the cells from each other and disperse them as a thin film monolayer. Dissociation may be accomplished by physical or enzymatic means. Similarly, dissociated cells in fluid samples or in scrapings may be concentrated and dispersed in a monolayer. In other instances, it may be desirable to concentrate disperse cells as a pellet. This can be accomplished by centrifugation of the liquid samples. Further processing includes chemical treatments such as fixation steps. Exemplary treatments include alcohol fixation. Suitable alcohols include methanol, ethanol, propanol, isopropanol, n-butanol and t-butanol.

Microscopic slides, typically glass or quartz, are prepared using the concentrated or processed specimen to optimize cellular content and, in a preferred embodiment, are stained with markers for DNA content and with stains or markers for additional cell characteristics such as CD34, CD31, annexin V, cytokeratin, CD19, CD36, CD44, KDR, CD45RO, BNH9, bcl-2 and a combination thereof. Preferred markers are CD34 and CD31.

VIII. Cell Staining

Characteristic molecules synthesized by tumors are often presented on the surface of tumor cells. Alternatively, cellular hallmarks such as DNA or nucleic acid, internal to the cell surface, may be stained with specific compounds. Stains, marker agents or antibodies directed to these surface molecules facilitate characterization of a cell being cancerous, characterization of a cell type, or characterization of blood vessels within the tissue.

A nonlimiting list of dyes contemplated in this invention include nucleic acid dyes such as acridine orange, 7-aminoactinomycin D, ethidium bromide, ethidium homodimer, LDS 751, propidium iodide, Syto 11, 12, 20, 22, 16, Syto 14, 15, 25, Syto 17, 59, 61, Sytox green, thiazole blue, thiazole orange, ToPro 1 , ToPro3; antibody labeling dyes for cell surface, cytoplasmic and nuclear antigens such as Alexa 488, APC, BODIPY FL, BODIPY 630/650, CY5, CY5.5, ECD, FITC, cytokeratin, hematoxylin-eosin, fluorescein-conjugated lectin, Ulex europaeus I (F-UEAI) counterstained with Harris hematoxylin, periodic acid-Schiff (PAS), bromodeoxyuridine, cathepsin B, Texas Red, rhodamine, cyanine, phycoerythrin, phycocyanin, allophycocyanin, o-phthaldehyde, fluorescamine, oregon green 488, PE, PE-APC, PE-CyS, PerCP, PE-TR, rhodamine green and rhodol green; cell metabolism dyes such as BCECF, calcium green, carboxy-DCF, carboxy SNARF-1 AM, DilCn5, DiOCn3, Fluo-3, Fura Red, Green Fluorescent Protein, JC-1 and NBD-C6-Ceramide; UV dyes such as Hoechst and Dapi. Other stains are known in the art may be used, and are summarized in references such as Bedrossian (1998), herein incorporated by reference. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

An advantage of the current invention in using LSC for observing the fluorescence signal is that fluorophores outside of the detectable range of the human eye can be used. Similarly, fluorophores with red emission maxima to close for the eye to accurately distinguish color can be used. A fluorescent label with an excitation wavelength capable of being excited by the fluorescent emission of another fluorescent dye is contemplated.

The cell nucleus may be stained by specific stains, such as propidium iodide or sytox green. In a specific embodiment propidium iodide is used. The propidium iodide, in a specific embodiment, is excited by a 488 nm wavelength argon-ion laser, and the red fluorescence emission is measured by appropriate detector.

The stains or markers may be visualized directly by fluorescence, light, color, radiation, etc., or they may be visualized indirectly, such as with antibody binding or secondary staining, such as with counterstaining. Cells can be visualized with anti-cytokeratin antibodies which bind to cytokeratin-expressing cells. In preferred embodiments monoclonal antibodies are conjugated to fluorescein isothiocyanate (FITC), phycoerythrin or PE/Cyanin 5.

There are a variety of commercial kits available for staining cells, such as those provided by Promega (Madison, Wis.) for in situ DNA nick end labeling (TUNEL) with terminal deoxynucleotidyl transferase enzymes. The fluorescence-based TUNEL method can be used as provided by the manufacture or modified. Modification of the labeling technique allows for higher signal-to-noise ratios and aids in the automation of quantification of LSC data to obtain the percentages of cell that undergo apoptosis.

Differences between apical and basal surfaces may be determined. Topography (morphology) of a specific cell may be smooth, asymmetrical, symmetrical, uneven, or marked with small or large pocks. Extensions on cells such as filopodia may be visualized.

In an embodiment of the present invention, fluorescence in situ hybridization (FISH) is utilized to analyze a cell characteristic. In this technique a fluorescently labeled nucleic acid probe preferentially hybridizes with a complementary nucleic acid sequence, or target nucleic acid, on one or more chromosomes in a cell. The target nucleic acid may be unique or repetitive, and in a preferred embodiment it is used to distinguish one or more specific chromosomes. The fluorescent label is detected by the LSC.

IX. Computer Programming and Data Processing

LSC, especially when several stains are used, can produce a large amount of raw data that, without the proper analysis, can be difficult to interpret. The development of FACS-based methods to detect multiple surface antigens simultaneously revolutionized the study of hematopoiesis and lymphopoiesis by allowing for detection of minor subpopulations in heterogeneous mixtures of cells. Fluorescent dyes with non-overlapping excitation and emission properties are now available that allow for simultaneous detection of up to 7 surface and/or intracellular antigens.

The LSC is an instrument in which tissue sections that are mounted on a solid surface (i.e., a glass microscope slide) are interrogated by a 5 μm-diameter argon laser that repeatedly scans along a line as the surface is moved past it on a computer-controlled motorized stage. TUNEL and/or immunostained cell preparations are then contoured by light scatter or counterstaining with a specific fluorescent dye, and fluorescence emissions within the contours are automatically processed by the software to generate a list of properties for the cells within that tissue. Thus, the LSC can be used very much like FACS to obtain two- and three-color fluorescence intensity information from a heterogeneous tissue specimen.

Although both the use of TUNEL and other immunohistochemical assays have been used to determine apoptosis and the use of vascular parameters have been used to determine the density of blood vessels, there has been no instance of both techniques used together to predict tumor responsiveness to a particular treatment protocol. The analysis of viable tumor cells, viable endothelial cells, tumor cell death, and blood vessel density in a single sample can be used as a biomarker for drug efficacy and prognostic indicator for patient survival.

The instant invention, uses a novel staining technique and a novel diagnostic application utilizing the LSC to collect data in an automated manner, and permits quantification of tumor cell death, endothelial cell death, and blood vessel density of a tumor sample. It would take weeks to collect the same amount of data manually, as the method of the instant invention collects in under five minutes. Automation of the procedure greatly reduces the amount of error and bias as well as human labor costs. Furthermore the instant invention can distinguish multiple fluorescent markers, not detectable by the human eye, especially in the same excitation wavelength.

Once the tissue is fluorescently stained, the scan area (tumor area) is selected by using CompuCyte's software to draw a gate around the tissue while visualizing the fluorescent image through the objective on the microscope. The selected area is then scanned by setting the instruments software to contour on the cell nuclei. The lasers and appropriate filters are selected in the instruments software-this is dependent on the fluorophores used for staining. In examples 2-7, the red, green, and long red filters are 'clicked on' for activation. The instrument can now be set to 'go' which begins the scanning process. The laser sensitivity is adjusted so that the pixels are not being saturated by the laser. The threshold contouring is set to maximize the number of events counted, such as cell nuclei. Once these parameters are set, the instrument scans and collects data.

After the scan is complete, the gates are set on the scattergram so that the collected data can be analyzed. Relocation of a cell is used to visualize which cells are positive, i.e. CD31 and/or TUNEL positive. Visualization allows the gate on the scattergram to be moved so that the positive cells fall in the appropriate quadrant. The data file can be replayed to obtain the number of cells in each quadrant that are representative of the total percent of all cells counted. The gating for TUNEL positive cells and for CD31 are demonstrated in FIGS. 2E and 3E. For BVD, the instruments software is set to contour on CD31 fluorescence. In Examples 2-7, this is by selecting the long red filter during the setup. The instrument then scans the same area but counts the number of blood vessels, i.e. a single vessel is counted by contiguous fluorescent light. Once the scan is complete, the total number of blood vessels is obtained and is displayed as the cell count. BVD can be calculated for that sample by dividing the blood vessel count by the total number of tumor endothelial cells. Endothelial cell density is determined by dividing the total number of endothelial cells by the total number of tumor cells.

Another method for obtaining data contemplated in this invention is the use of three separate contouring processes. After the tissue is fluorescently stained, the scan area is selected and the apoptotic cells are contoured. Stains such as Sytox green can be used. A separate scan in the same area is used to contour in the cell nuclei, using a different fluorophore (i.e. TUNEL). A third scan then counts the number of blood vessels. This method, using three scans instead of two, is advantageous because the dyes used (Sytox green and FITC from TUNEL), can give cleaner data. An extra instrument scan is necessary when the emission spectra of the dyes overlap to an extent to make separating the signals difficult.

Also contemplated in this invention is the addition of a software-assisted contouring in which the computer adjusts the contrast of the tissue map. This would reduce any user bias associated with this step of the invention.

X. Kits

Any of the compositions described herein may be comprised in a kit. In a non-limiting example, the components needed to perform the immunofluorescent double-staining technique may be comprised in a kit. The kits will thus comprise, in suitable container means, fluorescent dyes, antibodies, secondary antibodies, buffers and washes.

The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the fluorophore and antibodies, additional agent, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The fluorophore and antibodies may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the fluorophore and antibodies are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

As used herein the specification, "a" or "an" may mean one or more. As used herein in the claim(s), when used in conjunction with the word "comprising", the words "a" or "an" may mean one or more than one. As used herein "another" may mean at least a second or more.

XI. EXAMPLES

The following example is included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

General Procedures

Tumor specimens or patient biopsies are obtained prior to and several time points post-treatment such as 1, 3, and 7 days or more. Tissue sections are stained using an immunofluorescent double-labeling technique which permits the simultaneous detection of endothelial cells and fluorescent markers of apoptosis such as TUNEL or caspase activity. The tissue sections are scanned by the LSC and cell data is collected by the instrument's software. For the first scan, the Wincyte software is setup by the user to contour on the cell nuclei based on propidium iodide staining. Contouring on the cell nuclei provides the total cell number of the tissue specimen and creates a 'tissue map' which permits selective gating of the tumor cells. In addition, contouring on the cell nuclei permits the software to identify endothelial cells (based on CD31 and/or CD34, Pharmingen, Inc., fluorescent staining) and/or TUNEL positive cells (based on fluorescent TUNEL, Promega, Inc.). This data provides information on endothelial cell death which is critical in evaluating the effects of anti-angiogenic agents or other treatments which may target the tumor vasculature. A substantial increase in endothelial cell death post-treatment will indicate drug efficacy to induce apoptosis in tumor endothelial cells. Subsequent to endothelial cell death is the decay of the tumor vasculature. For the second scan, the Wincyte software is setup by the user to contour on the blood vessels of the tumor. The contouring is based on the fluorescence of the endothelial cell markers (CD31 and/or CD34). This data provides the total number of blood vessels that make up the tumor vasculature. If the treatment targets the tumor vasculature, the number of blood vessels in the tumor will be dramatically lower post-treatment.

Example 2

Immunofluorescence Double Staining

Formalin-fixed, paraffin embedded sections (5 µm) are deparaffinized in xylene, rehydrated in alcohol, and transferred to phosphate-buffered saline (PBS). Antigen retrieval is performed with 200 µg/ml proteinase-K for 30 minutes at room temperature. Frozen tissue sections (8 µm) are fixed by sequential incubation with cold acetone, acetone plus chloroform (1:1), and acetone (5 minutes each). Although frozen sections are usually easier to stain, both frozen and paraffin sections are used because paraffin sections are more convenient for clinical analysis. Sections are washed three times with PBS (5 minutes each) and incubated for 20 minutes at room temperature with protein blocking solution containing 5% normal horse serum and 1% normal goat serum. The blocking solution is removed and the sections are incubated for 24 hours at 4° C. with a 1:400 dilution of rat monoclonal anti-mouse CD31 antibody. Staining conditions may have to be optimized for some of the new reagents. Tissue sections are washed once with PBS containing 0.01% Brij and twice with PBS (5 minutes each). Sections were then incubated with protein blocking solution for 10 minutes at room temperature. Subsequent steps are performed in the dark. The blocking solution is removed and the sections are incubated with a 1:400 dilution of Texas Red-conjugated goat anti-rat secondary antibody (Jackson ImmunoResearch Laboratory, Inc., West Grove, Pa.) for 1 hour at room temperature. Sections are washed twice with PBS containing 0.2% Triton X-100 and once with PBS (5 minutes each). Tissue sections are fixed with 4% paraformaldehyde (methanol-free) for 10 minutes at room temperature.

TUNEL is performed using a commercial kit (Promega, Madison, Wis.) with the following modifications. The sections are washed with PBS two times (5 minutes each) and incubated with equilibration buffer (from Promega) for 10 minutes at room temperature. The equilibration buffer is removed and reaction buffer containing equilibration buffer, nucleotide mix, and terminal deoxynucleotidyl transferase (TdT) enzyme is added to the tissue sections (according to Promega). Slides are incubated for 1 hour at 37° C. in a dark humid atmosphere. The TUNEL reaction is terminated by immersing the slides in 2×SSC for 10 minutes. Sections are washed three times (5 minutes each) to remove unincorporated fluorescein-dUTP. For counterstaining total cell nuclei, the sections are incubated with 300 µg/ml of Hoechst #33342 stain (Polysciences, Inc., Warrington, Pa.) for 10 minutes at room temperature. The sections are washed twice with PBS (5 minutes each). To prevent bleaching, prolong (Molecular Probes, Eugene, Oreg.) is used to mount coverslips.

An exemplary procedure for immunofluorescence double staining was also done by Shaheen et al. (1999), incorporated herein by reference.

Example 3 laser Scanning Cytometry

Immunofluorescence microscopy is performed on an epifluorescence microscope equipped with narrow bandpass excitation filters mounted in a filter wheel to individually select for green, red, and blue fluorescence. Images are captured using a cooled CCD camera and SmartCapture software. Images are further processed using Adobe Photoshop software.

The LSC (CompuCyte, Corporation, Cambridge, Mass.) is an instrument designed to enable fluorescence-based quantitative measurements on tissue sections or other cellular preparations at the single cell level. The instrument consists of a base unit containing an Olympus BX50 fluorescent microscope and an optics/electronics unit coupled to argon and HeNe laser support elements and a computer. Tissue sections that are mounted on a solid surface (i.e., a glass microscope slide) are interrogated by a 5 µm-diameter argon laser that repeatedly scans along a line as the surface is moved past it on a computer-controlled motorized stage. TUNEL and/or immunostained cell preparations are then contoured by light scatter or counterstaining with a specific fluorescent dye, and fluorescence emissions within the contours are automatically processed by the software to generate a list of properties for the cells within that tissue. Thus, the LSC can be used very much like FACS to obtain two- and three-color fluorescence intensity information from a heterogeneous tissue specimen.

Example 4

Mouse Tumor

Survival signaling in tumor ECs were analyzed with immunofluorescence experiments in which pancreatic tumor xenografts from untreated or VEGF receptor antagonist-treated mice were stained with anti-CD31 and anti-phospho-ERK antibodies.

The isolation and functional characterization of the highly metastatic COLO-357 (Meitner et al., 1983) derivative, L3.6p1, have been described previously (Bruns et al., 1999). This cell line will be used to generate intra-pancreatic tumor xenografts. Male athymic nude mice (Balb/c background) are anesthetized with methoxyfurane. A small incision is made in the left abdominal flank and the spleen is exteriorized. A 40 µl cell suspension containing $1 \times 10^6$ cells is injected subcapsularly into the pancreas, and the abdominal wound is closed in one layer with wound clips (Bruns et al., 1999). Tumor incidence and rates of lymph node metastasis in control animals are 100%, and approximately 50% of animals develop liver metastases (Bruns et al., 1999; Bruns et al., 2000). Animals are sacrificed when controls become moribund. Primary tumors in the pancreas are excised and weighed. One part is snap-frozen in liquid nitrogen and stored at −80° C., and another part is formalin-fixed and embedded in paraffin. Lymph nodes and livers are harvested, weighed, and embedded in paraffin. In some experiments, control tissues (i.e., kidney, lung) will be harvested to measure rates of endothelial cell death in normal vasculature Results demonstrate that the instant invention can produce accurate and reliable data. The results demonstrate significant endothelial cell death occurs following treatment with an anti-angiogenic agent, SU6668 (currently in clinical trials), in a mouse liver metastasis model. The immunofluorescent double staining technique allows tumor specimens to be quantitated by the LSC in an automated manner. Treated and untreated mouse tumors were analyzed for endothelial cell death, tumor cell death, and blood vessel density. SU6668, which is currently in clinical trials was used with a mouse liver metastasis model. FIG. 1 represents a sample tissue after immunofluorescent double staining.

Figure 3:
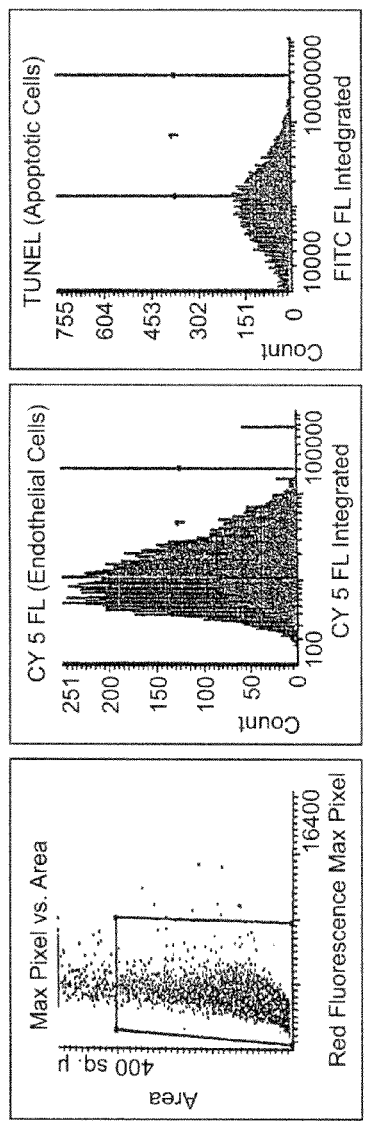
FIGS. 3 A-E—LSC scan of a treated mouse tumor.
Figure 3:
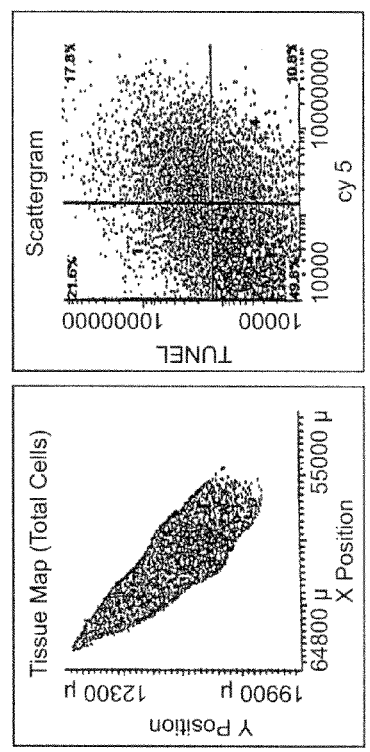
Figure 4:
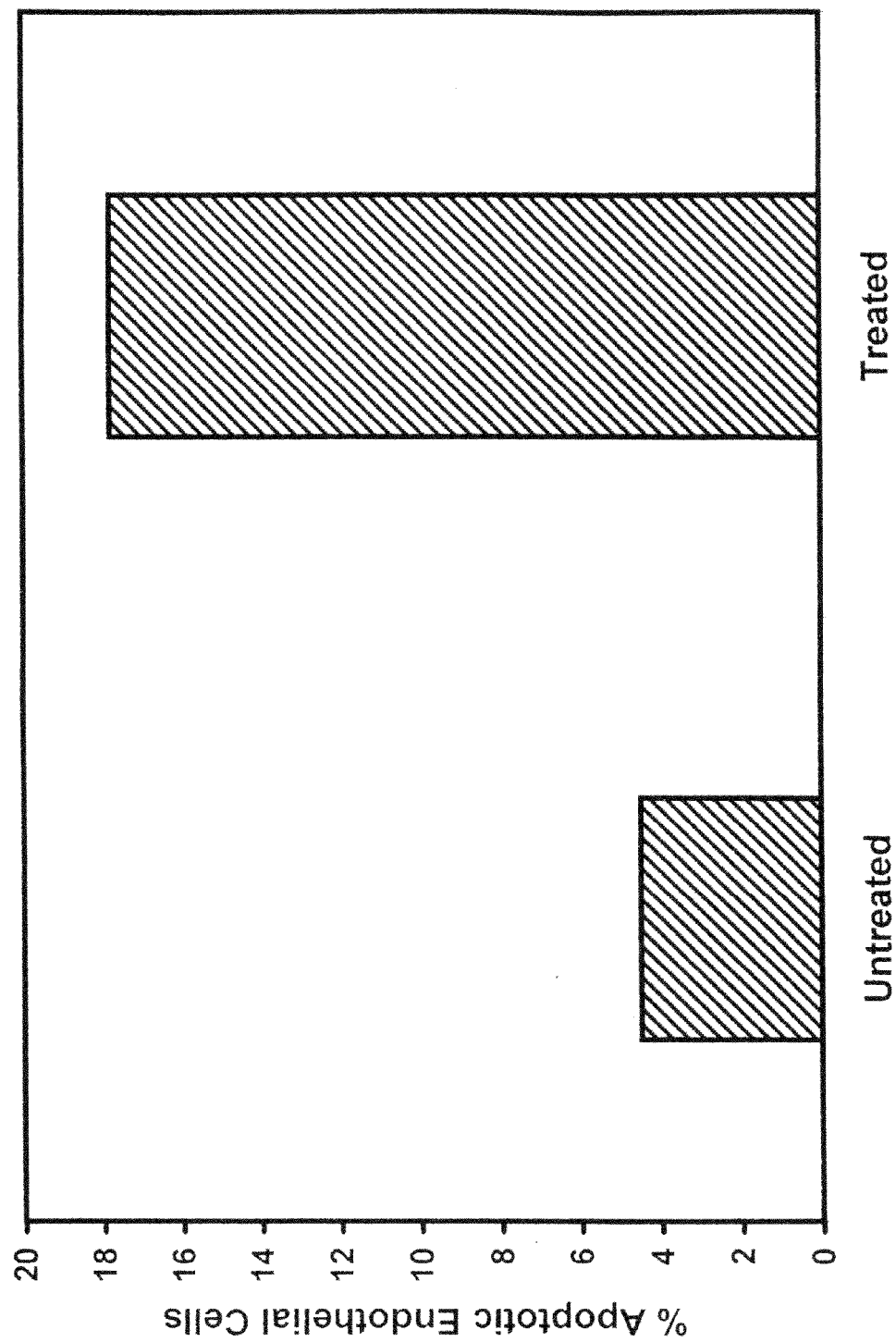
FIG. 4—Bar graph showing the percent apoptotic endothelial cells for the pre-clinical tumors scanned in FIGS. 2 and 3.

Untreated mouse tumor tissue was stained using immunofluorescent double staining and scanned with LSC to determine the number of apoptotic tumor and endothelial cells (FIG. 2). This requires contouring on the cell nuclei. The total cell nuclei is recorded as the "Number of cells in file" and can be found in the "Cell File Comments" box located on the LSC data print out. A 'tissue map' is created following the completion of the scan (FIG. 2D). Selective gating can be done on the tissue map to analyze a particular region of cells. Quantitative measurements of tumor EC apoptosis following therapy of colon cancer liver metastases with SU-6668 is shown in FIGS. 2E and 3E. In this FIG., EC apoptosis across the whole tumor section was quantified. The quadrants set in FIG. 2E provide the number of apoptotic tumor cells (I) and apoptotic endothelial cells (II). The gating set in FIG. 2E is based on fluorescent properties of the cells which can be found in FIG. 2B for endothelial cells and FIG. 2C for TUNEL positive cells. FIG. 3 represents data collected by the LSC on a treated mouse tumor. In vivo results showing the percent of total cells obtained from quadrant II on FIGS. 2E and 3E are in FIG. 4.

Figure 5:
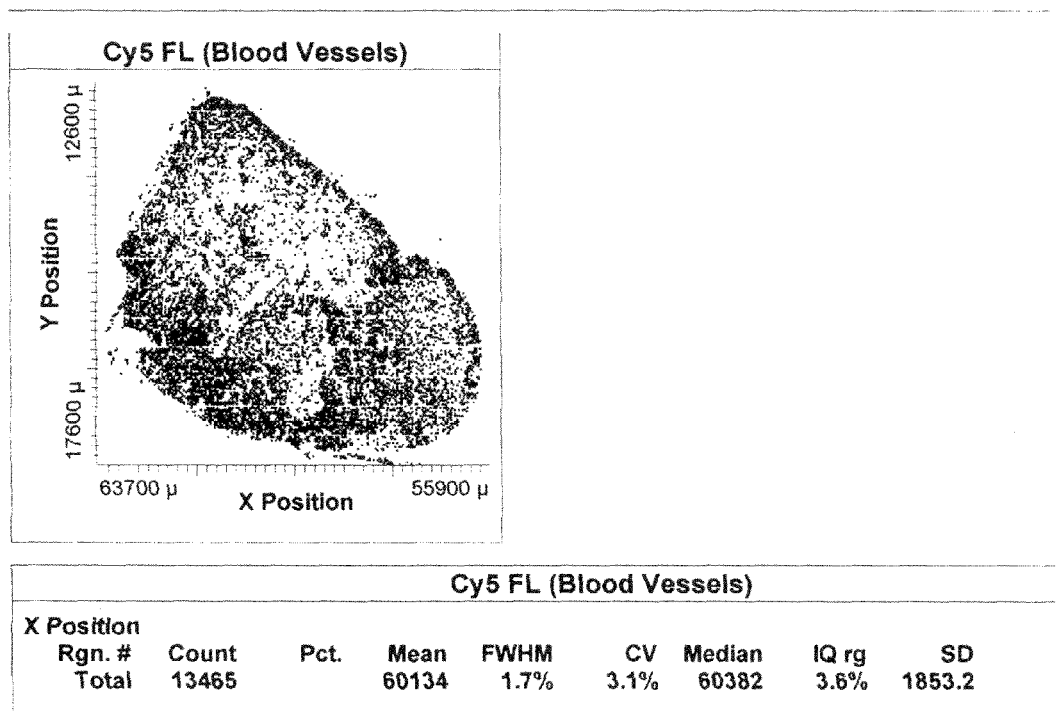
FIG. 5—LSC-mediated blood vessel contouring on an untreated mouse tumor, labeled with Cy5. Blood vessel density calculated is 52%.
Figure 6:
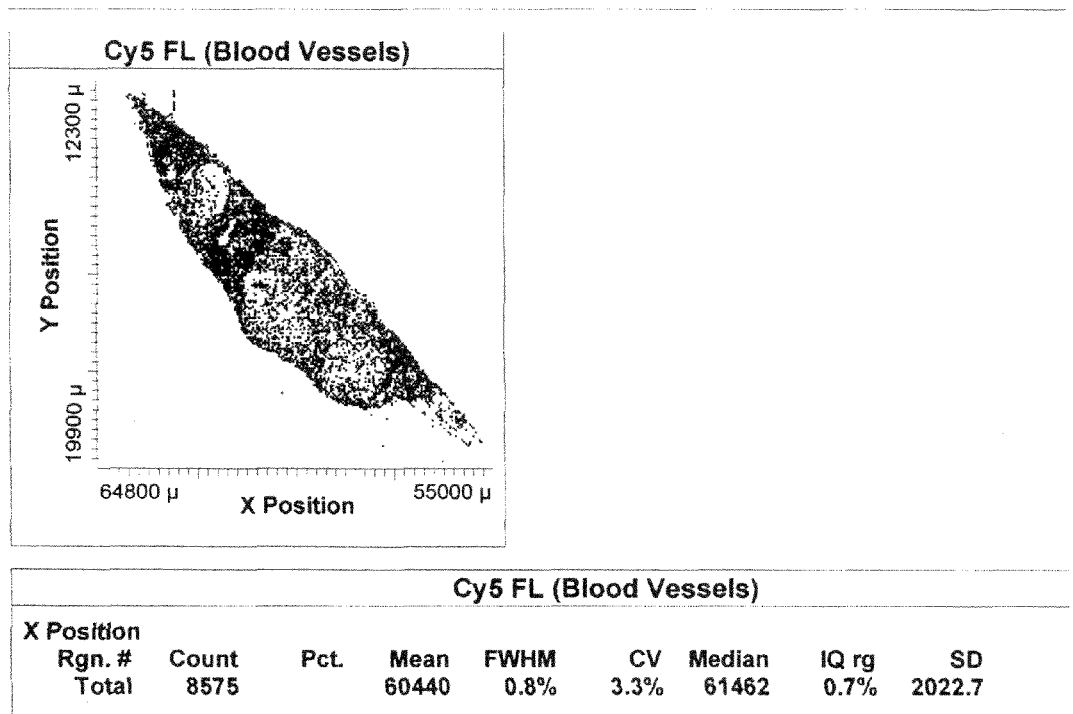
FIG. 6—LSC-mediated blood vessel contouring on a treated mouse tumor, labeled with Cy5. Blood vessel density calculated is 55%.

Because of limitations of the software, a second contouring was performed to quantitate blood vessel density on the same tissue specimens. The contouring is set to detect fluorescence of endothelial cells (CD31 and/or CD34). Any break in the fluorescent light will be counted as a single 'vessel.' FIG. 5 represents LSC-mediated blood vessel contouring on an untreated mouse tumor. The total number of blood vessels is recorded as the "Number of cells in file" located in the "Cell File Comments" box at the top of the LSC data print out. FIG. 6 represents LSC-mediated blood vessel contouring on a treated mouse tumor. The 'blood vessel density' of the tumor can be calculated using the total number of blood vessels in the tumor divided by the total number of cells obtained from the first scan. The untreated mouse tumor had a blood vessel density of 52% and the treated mouse tumor had a blood vessel density of 55%. If the therapy was effective at targeting the tumor vasculature a decrease in the 'blood vessel density' would be expected.

Example 5

Human Studies

Figure 7:
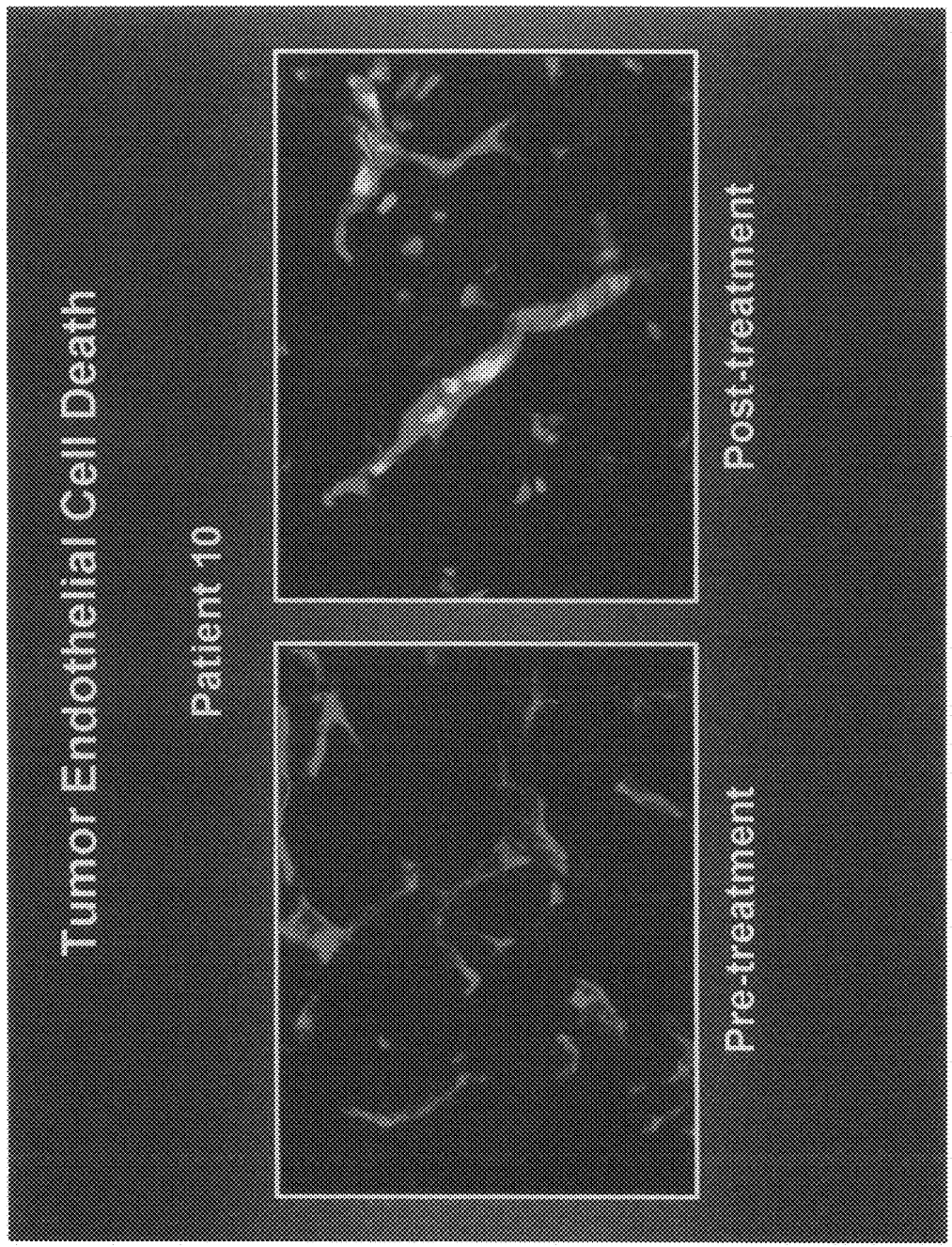
FIG. 7—Representative image of CD31(red) and TUNEL (green and yellow) in a human tumor biopsy specimen.
Figure 8:
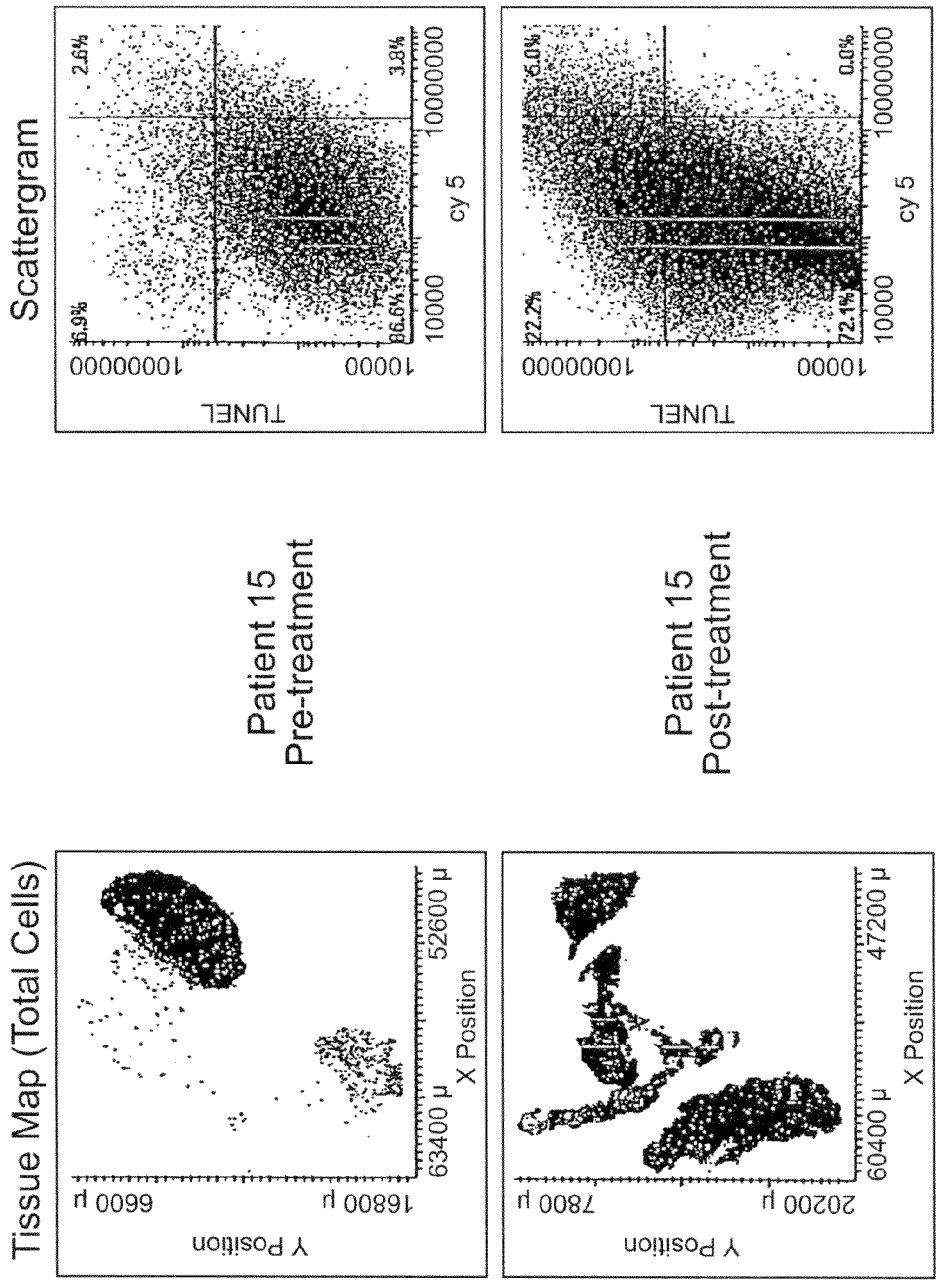
FIG. 8—LSC generated tissue map of cell nuclei and scattergram obtained from patient 15 biopsies stained with CD31/TUNEL pre and post-treatment with endostatin for two months.
Figure 9:
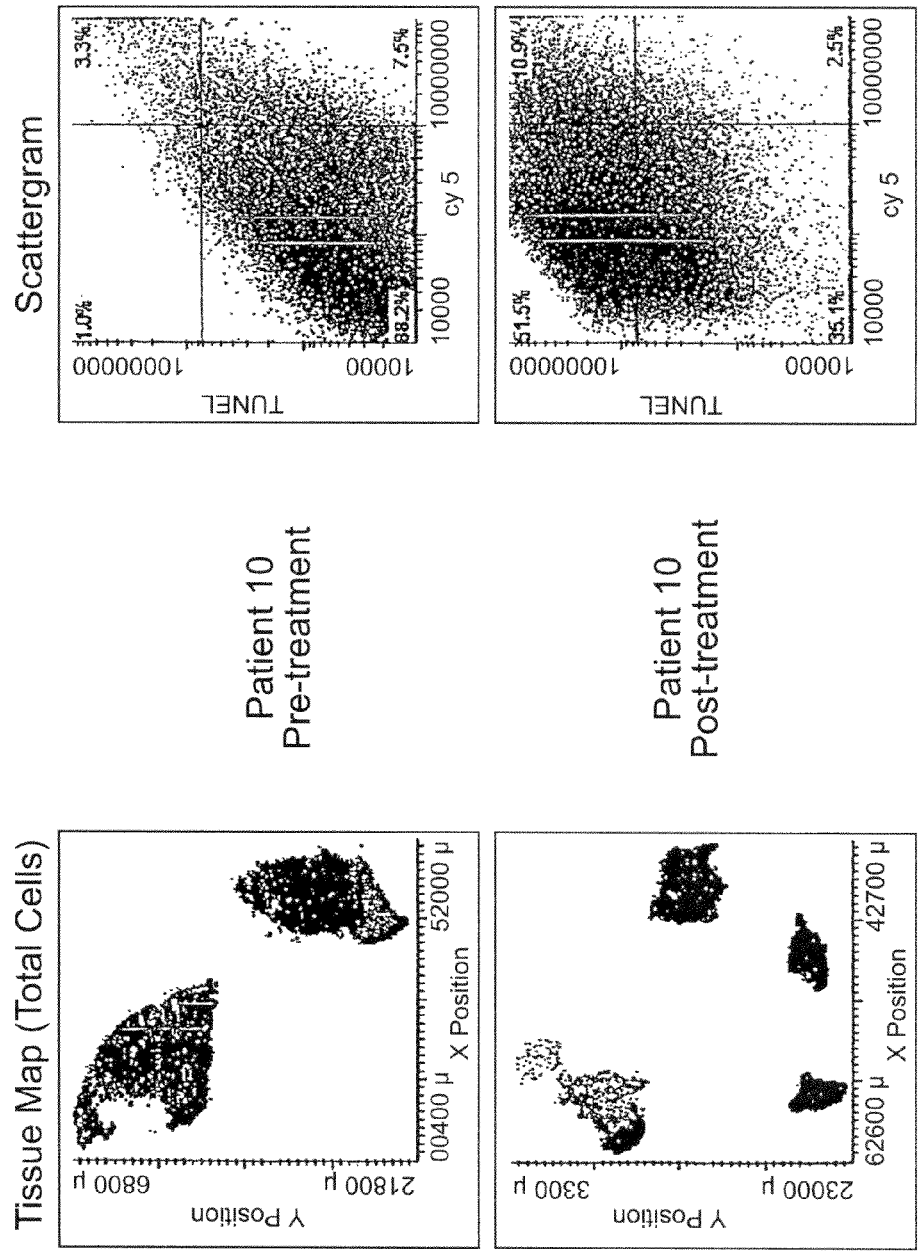
FIG. 9—LSC generated tissue map of cell nuclei and scattergram obtained from patient 10 biopsies stained with CD31/TUNEL pre and post-treatment with endostatin for two months.
Figure 10:
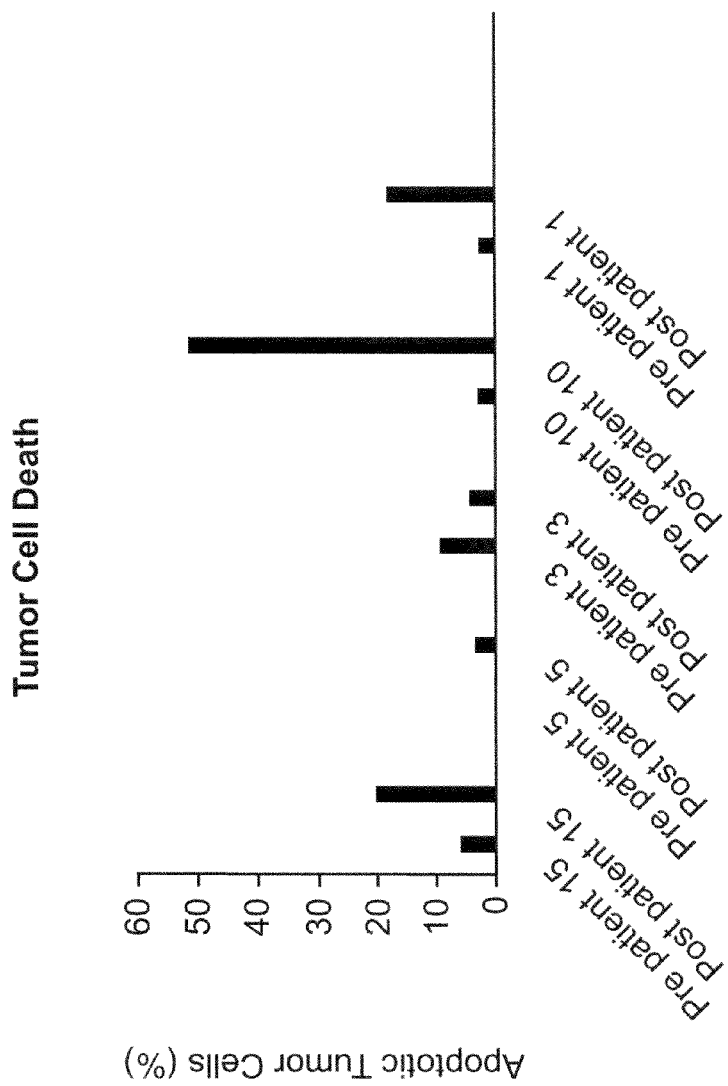
FIG. 10—Bar graph showing percent apoptotic tumor cells for five patients pre and post-treatment with endostatin.
Figure 11:
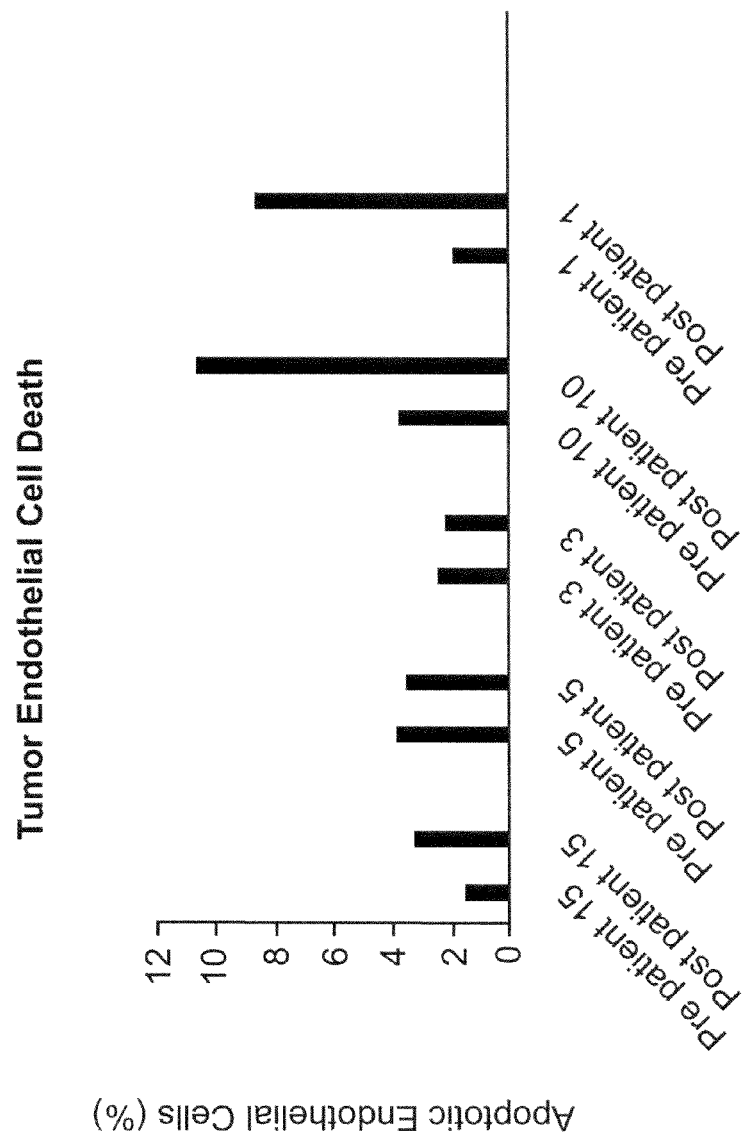
FIG. 11—Bar graph showing percent apoptotic endothelial cells before and after endostatin treatment.
Figure 12:
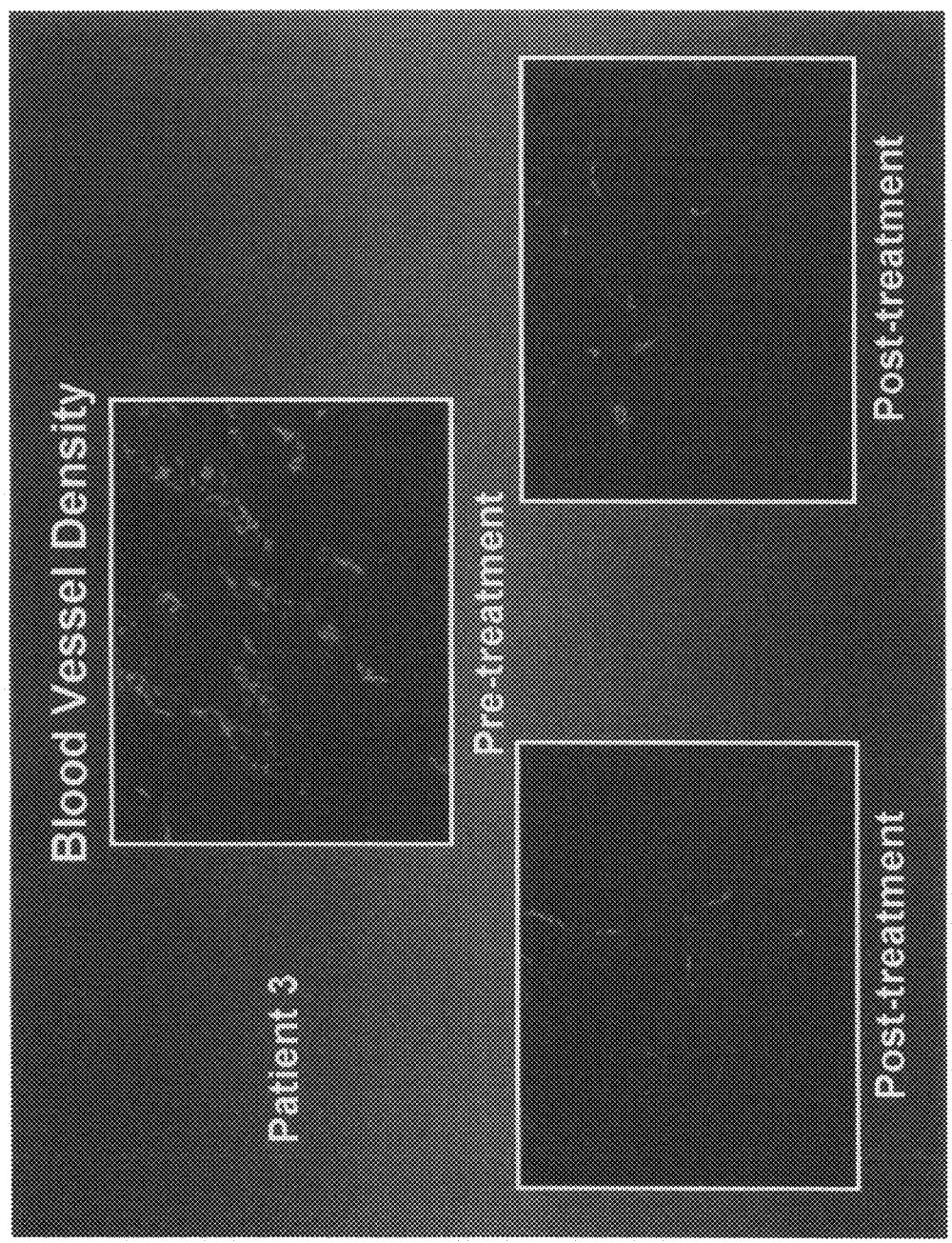
FIG. 12—Representative image of blood vessel staining (CD31) in a human biopsy tumor specimen.
Figure 12A:
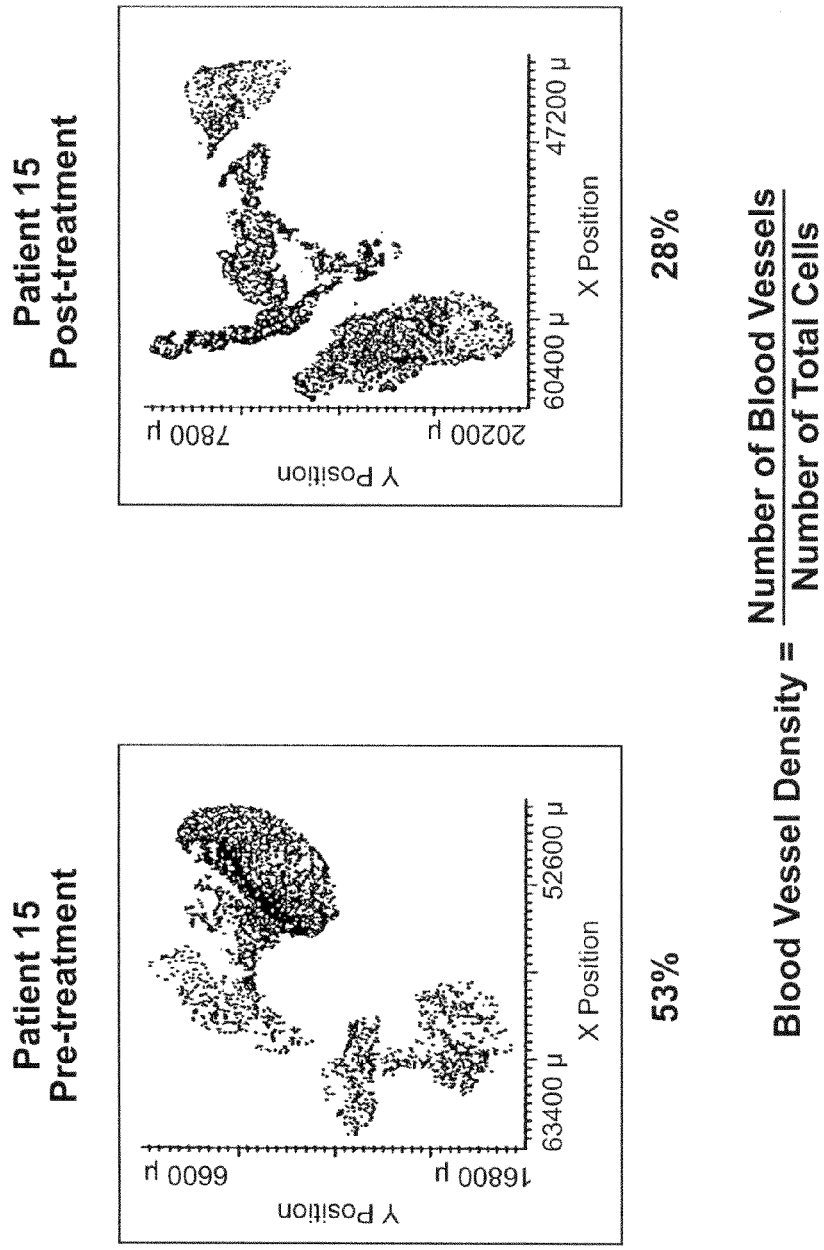
FIG. 12A—LSC-mediated blood vessel contouring of a patient biopsy pre and post-treatment with endostatin. Pre-treatment BVD=53%, post-treatment BVD=28%.
Figure 13:
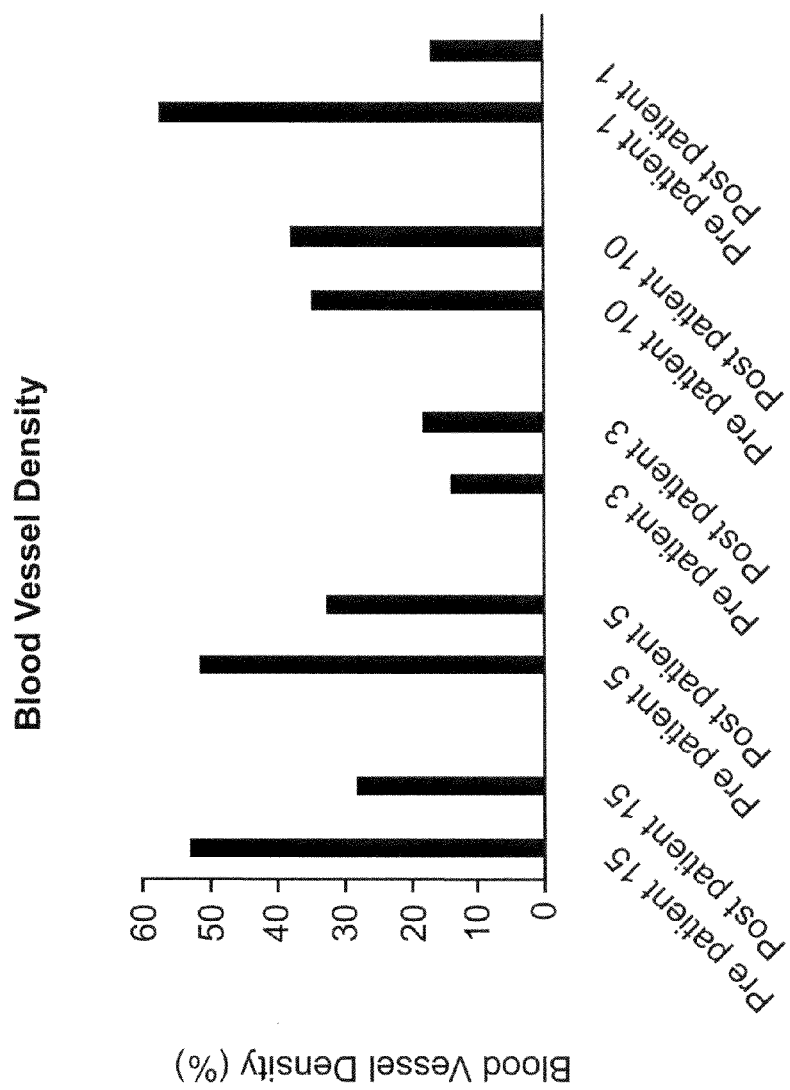
FIG. 13—Bar graph showing percent blood vessel density for five patients pre and post-treatment with endostatin.

A study of patients treated with endostatin for two months was done to demonstrate the feasibility of this technique for human subjects. Biopsies at different tumor sites were obtained from each of the five patients prior to and after treatment. The biopsies were stained with TUNEL and cy5 labeled antibody to CD31/CD32. FIG. 7 shows an image contoured to show the endothelial cell death of Patient 10. FIGS. 8-9 represent LSC data from two of the patients. The LSC-mediated analysis shown in FIG. 10 and FIG. 11 demonstrates that two out of four patients had a dramatic increase in apoptotic tumor and apoptotic endothelial cells. The data obtained from contouring on the blood vessels is shown in FIG. 12 where a representative image of blood vessel staining (CD31) is shown. A dramatic decrease in blood vessel density is shown by Patient 1 in FIG. 13.

Example 6

Efficacy of Standard Therapy on Breast Cancer

Figure 14:
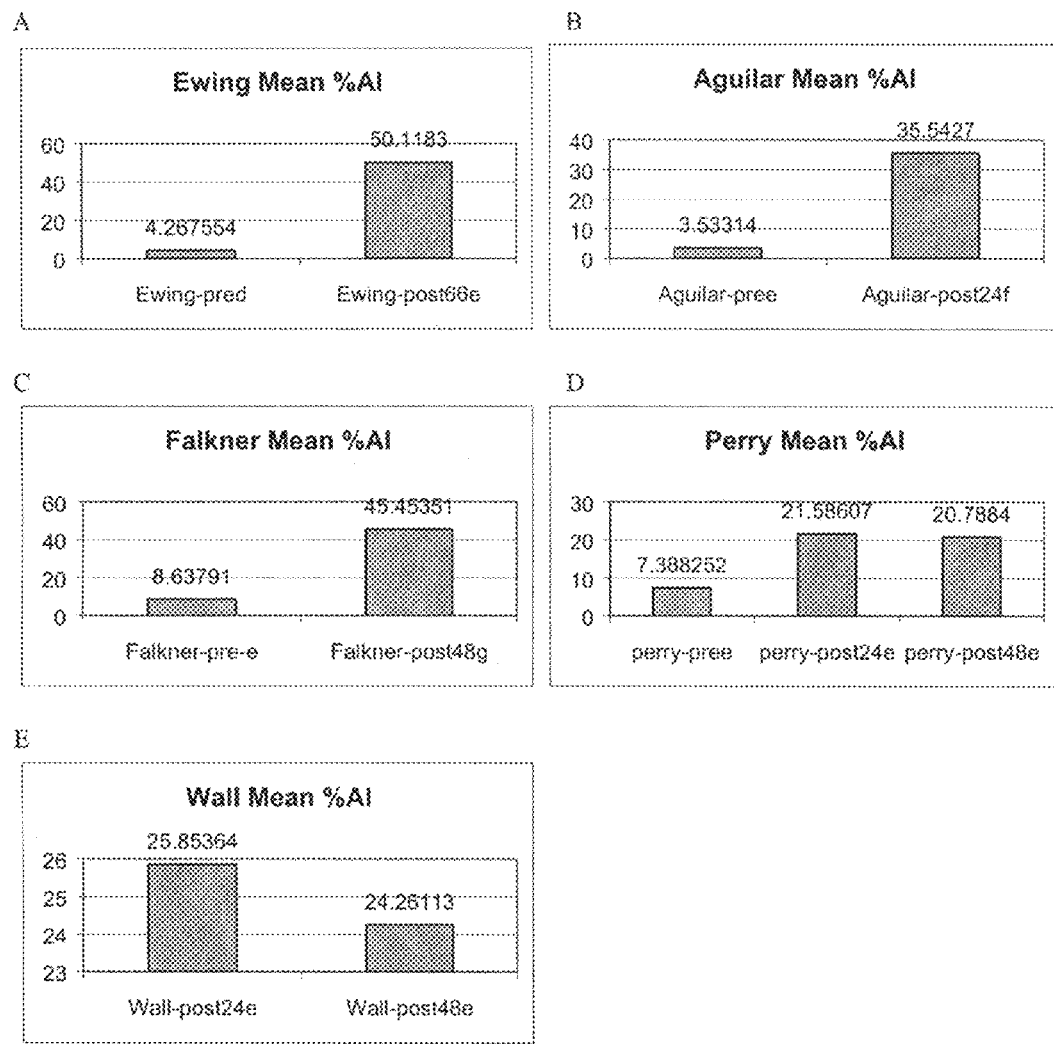
FIGS. 14A-E—Biopsies taken from breast cancer patients pre and post-treatment (24, 48, 66 hours) following neoadjuvant chemotherapy were processed and stained for fluorescent TUNEL. The number of TUNEL positive cells were counted and results are represented as a percent of total cells counted.
FIGS. 14F-H—Biopsies taken from breast cancer patients pre, 24, and 48 hours following neoadjuvant chemotherapy were processed and stained for fluorescent TUNEL.
Figure 14H:
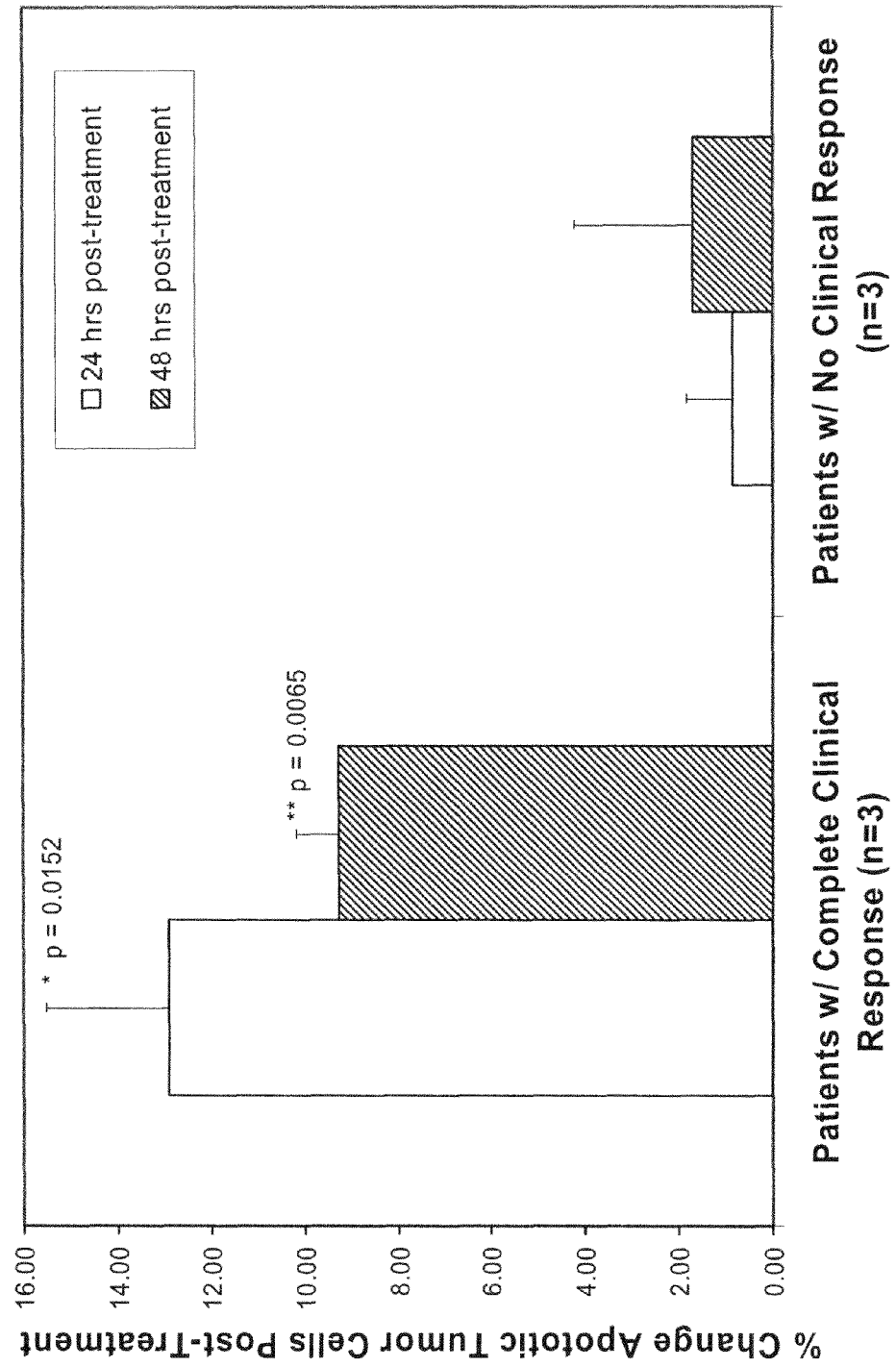

In addition to monitoring anti-angiogenic therapy, apoptosis levels in endothelial cells and tumor cells following neoadjuvant chemotherapy with taxol or docetaxel/doxorubicin were studied. A correlation of apoptosis with clinical outcome will have significant clinical relevance to the management of cancer. FIG. 14 demonstrates a dramatic increase in the number of apoptotic tumor cells following neoadjuvant chemotherapy in different patients with breast cancer. These data demonstrate feasibility of our technique to monitor apoptosis levels and have shown that patients are willing to undergo serial biopsies for the purpose of predicting their response in order to undergo the most appropriate therapy.

Example 7

Study of Endostatin Dosing

Figure 15A:
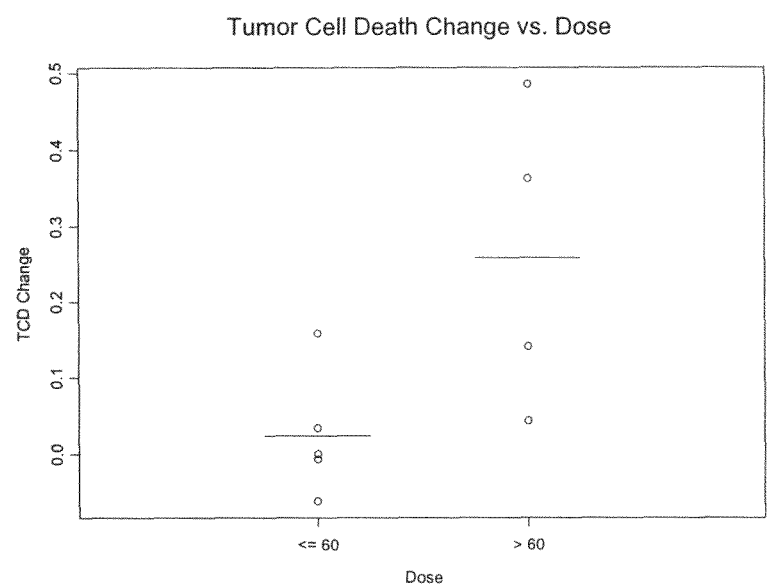
FIGS. 15A-C—Graphs showing effects of dosage (<60 mg, and >60 mg) on tumor cell death, tumor endothelial cell death, and blood vessel density for pre and post-treatment data with endostatin.
Figure 15B:
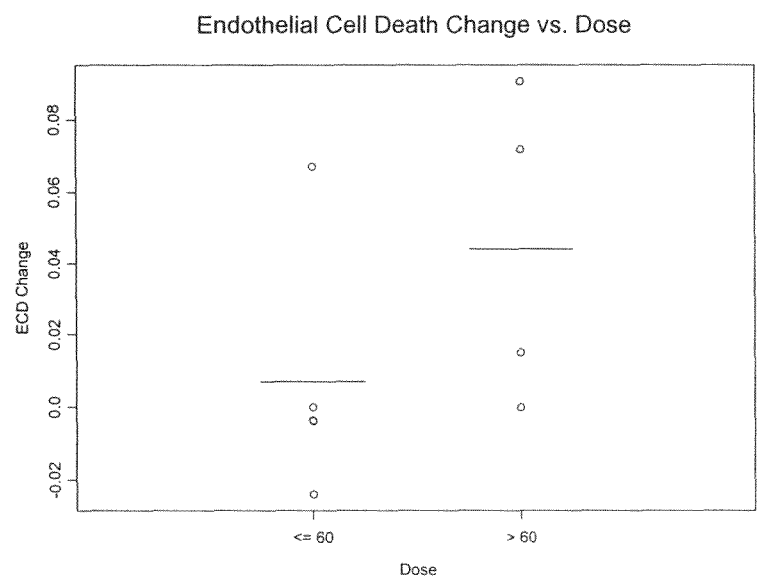
Figure 15C:
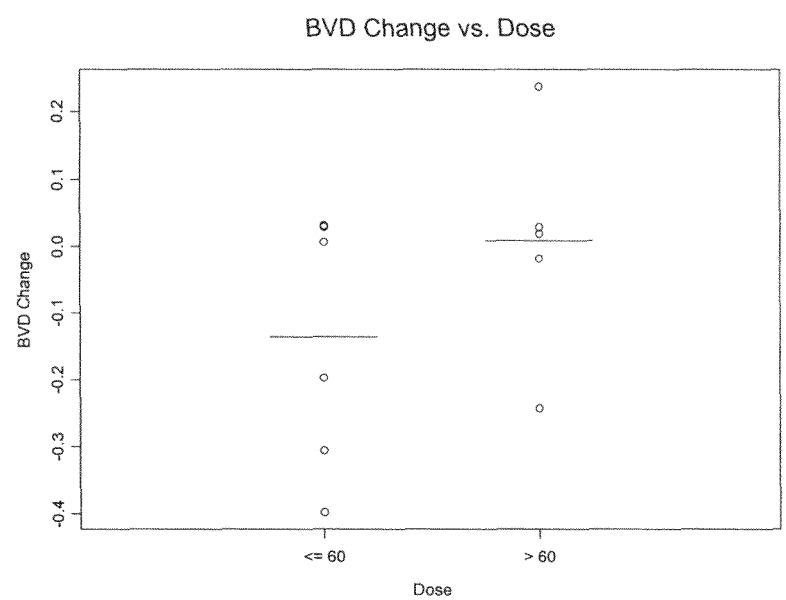
Figure 15D:
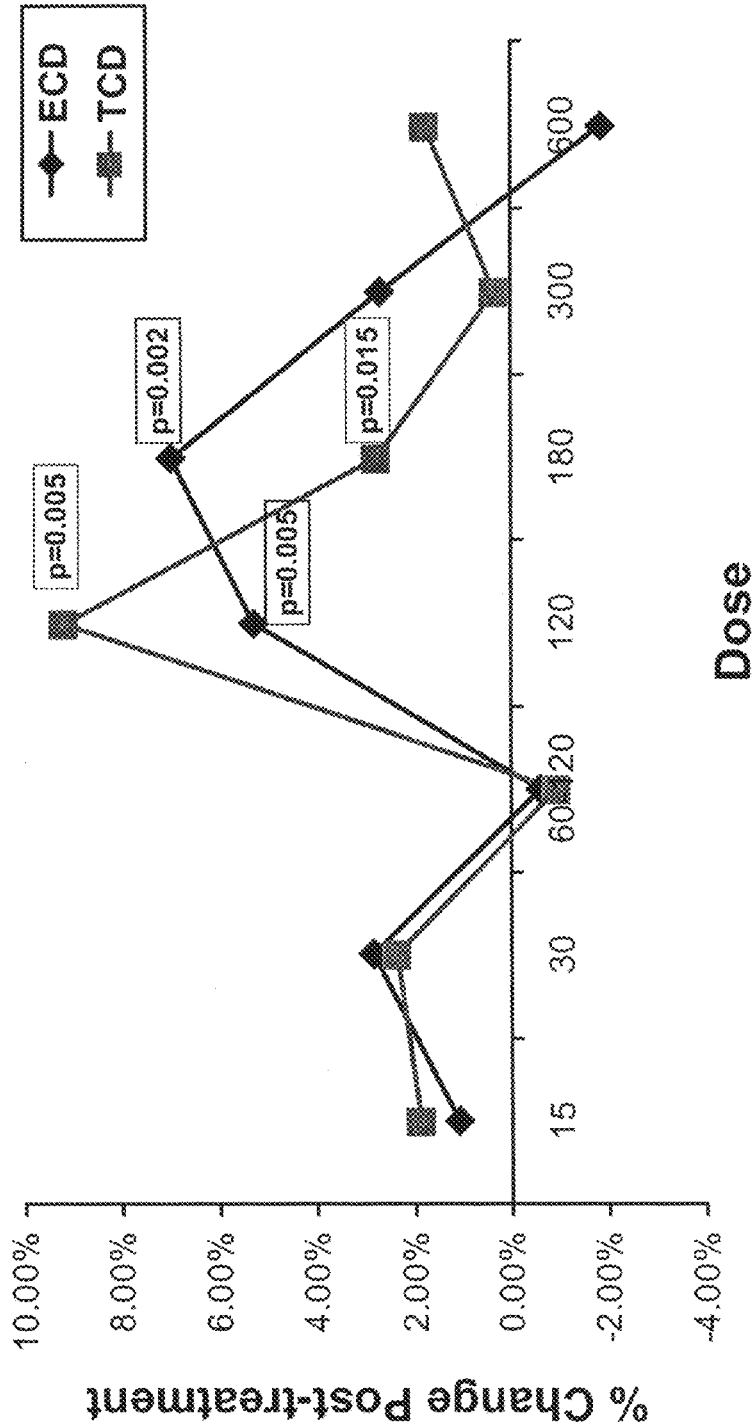
FIG. 15D—Shows the percentage change in tumor cell death following various endostatin doses.

The effect of dosing on tumor cell death, endothelial cell death, and BVD is shown in FIGS. 15A-C. FIG. 15A shows tumor cell death data where, at a dose of <60 mg, a change of 0.02 was seen where at a dose of >60 mg, a change of 0.26 was seen. This gives a difference of 0.23. The 95% CI for this difference is (0.00,0.47), p=0.050 and is significant. The values obtained for tumor endothelial cell death and blood vessel density were not significant in this study.

Example 8

Correlation Between Endothelial Cell Death and Tumor Cell Death

Figure 16:
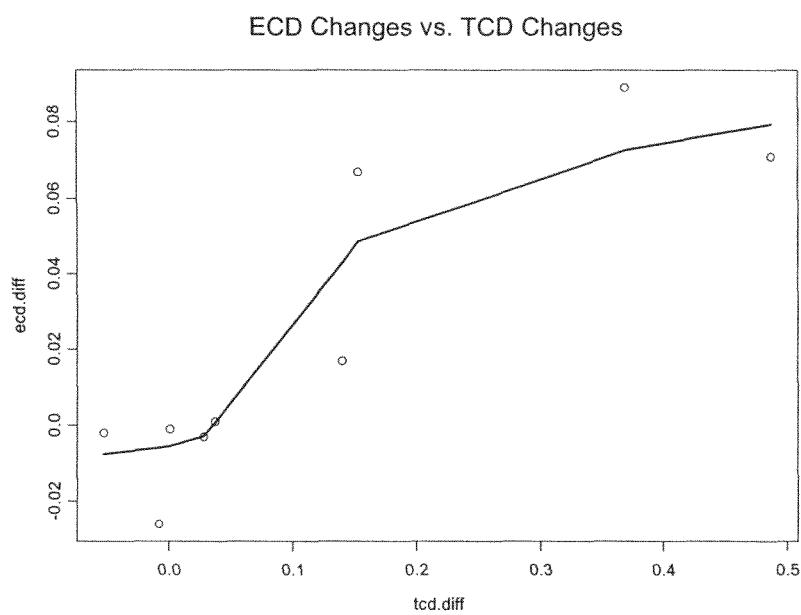
FIG. 16—Graph of endothelial cell death in a sample compared to tumor cell death, demonstrating that endothelial cell death and tumor cell death are highly correlated.
Figure 17A:
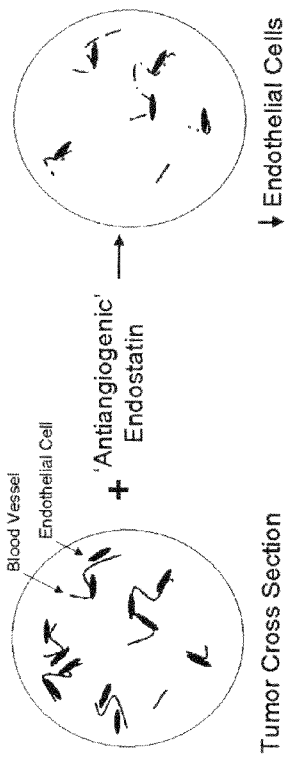
FIGS. 17A-B—FIG. 17A Is a diagram showing the concept of quantifying endothelial cells in a tumor biopsy using the LSC. The LSC is used to count endothelial and tumor cells independently in a biopsy. Endothelial cell density (ED) is calculated by dividing the total number of endothelial cells by the total number of tumor cells.
Figure 17B:
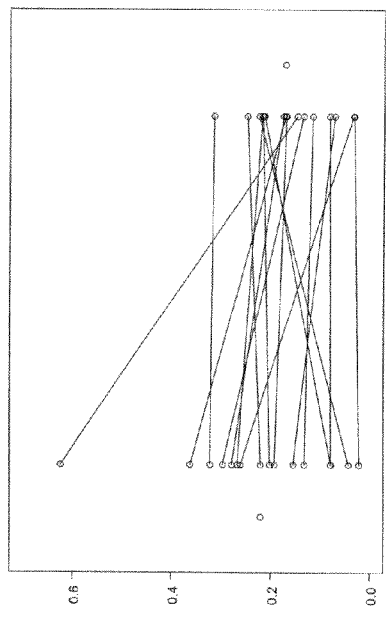

FIG. 16 demonstrates a correlation between endothelial cell death and tumor cell death in LSC data obtained for patients treated with endostatin. These data are highly correlated, supporting a therapeutic endpoint. BVD for the pre-treatment sample is 53% while BVD for the post-treatment sample is 28%.

REFERENCES

The following references, to the extent that they provide exemplary procedural or other details supplementary to those set forth herein, are specifically incorporated herein by reference.

Arap, W., Pasqualini, R., and Ruoslahti, E. "Cancer treatment by targeted drug delivery to tumor vasculature in a mouse model", Science. 279: 377-80, 1998.

Bedrossian, C W M. Special stains, the old and the new: the impact of immunocytochemistry in effusion cytology. Diagnostic Cytopathology 1998; 18(2): 141-149.

Bergers, G., Javaherian, K., Lo, K. M., Folkman, J., and Hanahan, D. Effects of angiogenesis inhibitors on multistage carcinogenesis in mice, Science. 284: 808-12, 1999.

Blankenberg, F. G., Katsikis, P. D., Tait, J. F., Davis, R. E., Naumovski, L., Ohtsuki, K., Kopiwoda, S., Abrams, M. J., Darkes, M., Robbins, R. C., Maecker, H. T., and Strauss, H. W. In vivo detection and imaging of phosphatidylserine expression during programmed cell death, Proc Natl Acad Sci U S A. 95: 6349-54, 1998.

Boehm, T., Folkman, J., Browder, T., and O'Reilly, M. S. Antiangiogenic therapy of experimental cancer does not induce acquired drug resistance, Nature. 390: 404-407, 1997.

Bruns, C. J., Harbison, M. T., Kuniyasu, H., Eue, I., and Fidler, I. J. In vivo selection and characterization of metastatic variants from human pancreatic adenocarcinoma by using orthotopic implantation in nude mice., Neoplasia. 1: 50-62, 1999.

Bruns, C. J., Shinohara, H., Harbison, M. T., Davis, D. W., Nelkin, G., Killion, J. J., McConkey, D. J., Dong, Z., and Fidler, I. J. Therapy of human pancreatic carcinoma implants by irinotecan and the oral immunomodulator JBT 3002 is associated with enhanced expression of inducible nitric oxide synthase in tumor-infiltrating macrophages [In Process Citation], Cancer Res. 60: 2-7, 2000.

Claesson-Welsh, L., Welsh, M., Ito, N., Anand-Apte, B., Soker, S., Zetter, B., O'Reilly, M., and Folkman, J. Angiostatin induces endothelial cell apoptosis and activation of focal adhesion kinase independently of the integrin-binding motif RGD, Proc Natl Acad Sci U S A. 95: 5579-83, 1998.

Clatch R J, Walloch J L, Zufter M M, Kamentsky L A. Immunophenotypic analysis of hematologic malignancy by laser scanning cytometry. Am J Clin Pathol 1996:105:744-755.

Clatch, Richard J.. Walloch. Jami L., Foreman, James R., and Kamentsky, Louis A. Multiparameter analysis of DNA content and cytokeratin expression in breast carcinoma by laser scanning cytometry. Arch Pathol Lab Med. 1997 Jun; 121(6): 585-92.

Cosgrove, D. O., Bamber, J. C., Davey, J. B., McKinna, J. A., Sinnett, H. D. "Color Doppler signals from breast tumors. Work in progress" Radiology, 1990, 176:175-80.

Dhanabal, M., Ramchandran, R., Waterman, M. J., Lu, H., Knebelmann, B., Segal, M., and Sukhatme, V. P. Endostatin induces endothelial cell apoptosis, J Biol Chem. 274: 11721-6, 1999.

Dong, C., Granville, D. J., Tuffnel, C. E., Kenyon, J., English, D., Wilson, J. E., McManus, B. M. "Bax and apoptosis in acute and chronic rejection of rat cardiac allografts" 1999, 79: 1643-53.

Fanelli, M.; Locopo, N., Gattuso, D., Gasparini, G. "Assessment of tumor vascularization: immunohistochemical and non-invasive methods" Int. J. Biol. Markers" 1999 14: 218-31.

Folkman, Cancer Res. 46, 467-473, 1986.

Folkman, N Engl J Med. 285(21): 1182-1186, 1971.

Folkman, N Engl J Med. 320(18): 1211-1212, 1989.

Folkman, J. and Klagsburn, M., Science 235:442, 1987.

Folkman et. al. Science, 235:442-447, 1987.

Fox, S. B., Leek, R. D., Weekes, M. P., Whitehouse, R. M., Gaffer, K. C., Harris, A. L. "Quantitation and prognostic value of breast cancer angiogenesis: comparison of microvessel denstiy, Chalkley count, and computer image analysis" J. Pathol 1995 177: 275-83.

Friedlander, M., Brooks, P. C., Shaffer, R. W., Kincaid, C. M., Varner, J. A., and Cheresh, D. A. Definition of two angiogenic pathways by distinct alpha v integrins, Science. 270: 1500-2, 1995.

Fujio, Y. and Walsh, K. Akt mediates cytoprotection of endothelial cells by vascular endothelial growth factor in an anchorage-dependent manner, J Biol Chem. 274. 16349-54, 1999.

Gavrieli, Y., Sherman, Y., and Ben-Sasson, S. A. Identification of programmed cell death in situ via specific labeling of nuclear DNA fragmentation, J. Cell Biol. 119. 493-501, 1992.

Gazit, Y., Baish, J. W., Safabakhsh, N., Leunig, M., Baxter, L. T., and Jain, R. K. Fractal characteristics of tumor vascular architecture during tumor growth and regression, Microcirculation. 4: 395-402, 1997.

Gerber, H. B., Dixit, V., and Ferrara, N. Vascular endothelial growth factor induces expression of the antiapoptotic proteins BCL-2 and A1 in vascular endothelial cells, J. Biol. Chem. 273: 13313-13316, 1998.

Grasl-Kraupp, B., Ruttkay-Nedecky, B., Koudelka, H., Bukowska, K., Bursch, W., and Schulte-Hermann, R. In situ detection of fragmented DNA (TUNEL assay) fails to discriminate among apoptosis, necrosis, and autolytic cell death: a cautionary note, Hepatology. 21: 1465-8, 1995.

Griffey, S. M., Verstraete, F. J., Kraegel, S. A., Lucroy, M. D., Madewell, B. R., "Computer-assisted image analysis of intratumoral vessel density in mammary tumors from dogs" Am. J. Vet Res. 1998, 59: 1238-42.

Gupta, K., Kshirsagar, S., Li, W., Gui, L., Ramakrishnan, S., Gupta, P., Law, P. Y., and Hebbel, R. P. VEGF prevents apoptosis of human microvascular endothelial cells via opposing effects on MAPK/ERK and SAPK/JNK signaling, Exp Cell Res. 247: 495-504, 1999.

Ikeda, H. Hirato, J, Akami, M., Suzuki, N., Takahashi, A., Kuroiwa, M., Matsuyama, S. "Massive apoptosis detected by in situ DNA nick end labeling in neuroblastoma" Am J. Surg. Pathol 1996, 20:649-655.

Kamentsky L A, Kamentsky L D. Microscope-based multiparameter laser scanning cytometer yielding data comparable to flow cytometry data. Cytometry 1991;12:381-387.

Karsan, A., Yee, E., Poirier, G. G., Zhou, P., Craig, R., and Harlan, J. M. Fibroblast growth factor-2 inhibits endothelial cell apoptosis by BCL-2-dependent and independent mechanisms, Am. J. Pathol. 151: 1775-1784, 1997.

Kerr, J. F. R., Wyllie, A. H., and Currie, A. R. Apoptosis: A basic biological phenomenon with wide-ranging implications in tissue kinetics., Br. J. Cancer. 26: 239-257., 1972.

Leunig, M., Yuan, F., Menger, M. D., Boucher, Y., Goetz, A. E., Messmer, K., and Jain, R. K. Angiogenesis, microvascular architecture, microhemodynamics, and interstitial fluid pressure during early growth of human adenocarcinoma LS174T in SCID mice, Cancer Res. 52: 6553-60, 1992.

Meitner, P. A., Kajiji, S. M., LaPosta-Frazier, N., Bogaars, H. A., Jolly, G. A., Dexter, D. L., Calabresi, P., and Turner, M. D. "COLO 357," a human pancreatic adenosquamous carcinoma: growth in artificial capillary culture and in nude mice, Cancer Res. 43: 5978-85, 1983.

Nor, J. E., Christensen, J., Mooney, D. J., and Polverini, P. J. Vascular endothelial growth factor (VEGF)-mediated angiogenesis is associated with enhanced endothelial cell survival and induction of Bcl-2 expression, Am J Pathol. 154: 375-84, 1999.

O'Reilly, M. S., Holmgren, L., Chen, C., and Folkman, J. Angiostatin induces and sustains dormancy of human primary tumors in mice, Nat Med. 2: 689-92, 1996.

O'Reilly, M. S., Boehm, T., Shing, Y., Fukai, N., Vasios, G., Lane, W. S., Flynn, E., Birkhead, J. R., Olsen, B. R., and Folkman, J. Endostatin: an endogenous inhibitor of angiogenesis and tumor growth, Cell. 88: 277-85, 1997.

Pasqualini, R. and Ruoslahti, E. Organ targeting in vivo using phage display peptide libraries, Nature. 380: 364-6, 1996.

Pasqualini, R., Koivunen, E., Kain, R., Landenranta, J., Sakamoto, M., Stryhn, A., Ashmun, R. A., Shapiro, L. H., Arap, W., and Ruoslahti, E. Aminopeptidase N is a receptor for tumor-homing peptides and a target for inhibiting angiogenesis., Cancer Res. in press:, 2000.

Rajotte, D., Arap, W., Hagedorn, M., Koivunen, E., Pasqualini, R., and Ruoslahti, E. Molecular heterogeneity of the vascular endothelium revealed by in vivo phage display, J Clin Invest. 102: 430-7, 1998.

Savill, J., Fadok, V., Henson, P., and Haslett, C. Phagocytic recognition of cells undergoing apoptosis., Immunol. Today. 14: 131-136., 1993.

Schlingemann, R. O., Rietveld, F. J., de Waal, R. M., Ferrone, S., and Ruiter, D. J. Expression of the high molecular weight melanoma-associated antigen by pericytes during angiogenesis in tumors and in healing wounds, Am J Pathol. 136: 1393-405, 1990.

Seifert, W. F., Verhofstad, A. A., Wobbes, T., Lange, W., Rijken, P. F., van der Kogel, A. J., Hendriks, T. "Quantitation of angiogenesis in healing anastomoses of the rat colon" Exp. Mol Pathol, 1997, 64:31-40.

Shabisgh, A., Tanji, N., D'Agati V., Burchardt, M., Rubin, M., Goluboff, E. T., Heitjan, D., Kiss, A., Buttyan, R. "Early effects of castration on the vascular system of the rat ventral prostate gland"1999, 140:1920-6.

Shaheen, R. M., Davis, D. W., Liu, W., Zebrowski, B. K., Wilson, M. R., Bucana, C. D., McConkey, D. J., McMahon, G., Ellis, L. M. "Antiangiogenic therapy targeting the tyrosin kinase receptor for vascular endothelial growth factor receptor inhibits the growth of colon cancer liver metastasis and induces tumor and endothelial cell apoptosis" Cancer Research, 1999. 59: 5412-5416.

Spyridopoulos, I., Brogi, E., Kearney, M., Sullivan, A. B., Cetrulo, C., Isner, J. M., and Losordo, D. W. Vascular endothelial growth factor inhibits endothelial cell apoptosis induced by tumor necrosis factor-alpha: balance between growth and death signals [published erratum appears in J Mol Cell Cardiol 1998 Apr; 30(4): 897], J Mol Cell Cardiol. 29: 1321-30, 1997.

Stephens, L. C., Ang, K. K., Schultheiss, T. E., Milas, L., and Meyn, R. E. Apoptosis in irradiated murine tumors, Radiat Res. 127: 308-16, 1991.

Svanberg, Cancer, 35:1382, 1975.

Tran, J., Rak, J., Sheehan, C., Saibil, S. D., LaCasse, E., Korneluk, R. G., and Kerbel, R. S. Marked induction of the IAP family antiapoptotic proteins survivin and XIAP by VEGF in vascular endothelial cells, Biochem Biophys Res Commun. 264: 781-8, 1999.

Visscher, D. W., Smilanetz, S., Drozdowicx, S, Wykes, S. M. "Prognostic significance of image morphometric microvessel enumeration in breast carcinoma" Anal. Quant. Cytol. Histol 1993; 15: 88-92.

Vu, T. H., Shipley, J. M., Bergers, G., Berger, J. E., Helms, J. A., Hanahan, D., Shapiro, S. D., Senior, R. M., and Werb, Z. MMP-9/gelatinase B is a key regulator of growth plate angiogenesis and apoptosis of hypertrophic chondrocytes, Cell. 93: 411-22, 1998.

Watanabe, Y. and Dvorak, H. F. Vascular permeability factor/vascular endothelial growth factor inhibits anchorage-disruption-induced apoptosis in microvessel endothelial cells by inducing scaffold formation, Exp Cell Res. 233: 340-9, 1997.

Wiedner, N., Amer. J. Path. 147: 9-19, 1995.

Weidner, Carroll, Flax et al., "Tumor angiogenesis correlates with metastasis in invasive prostate carcinoma, *Am. J. Pathol.*, 143:401-409, 1993.

Weidner, Semple, Welch, "Tumor angiogenesis and metastasis-correlation in invasive breast carcinoma," *N. Engl. J. Med.*, 324:1-8, 1991.

Yin, X. M., Wang, K., Gross, A., Zhao, Y., Zinkel, S., Klocke, B., Roth, K. A., and Korsmeyer, S. J. Bid-deficient mice are resistant to Fas-induced hepatocellular apoptosis, Nature. 400: 886-91, 1999.

U.S. Pat. No. 6,009,342
U.S. Pat. No. 5,688,694
U.S. Pat. No. 5,942,385
U.S. Pat. No. 5,942,385
U.S. Pat. No. 5,840,507
U.S. Pat. No. 6,009,342
U.S. Pat. No. 5,427,910
U.S. Pat. No. 5,793,969
U.S. Pat. No. 5,885,840

The invention claimed is:

1. A method for predicting anti-cancer therapeutic efficacy in an animal with a cancerous tumor comprising:
    a) obtaining a cancer tumor tissue sample from an animal subject undergoing anti-cancer therapy;
    b) staining said sample with at least one fluorescent label, wherein the at least one fluorescent label stains nuclei;
    c) subjecting said sample to laser scanning cytometry; and
    d) obtaining data on the number of apoptotic tumor-associated endothelial cells and blood vessel density in said sample,
wherein predicting anti-cancer therapeutic efficacy is determined by comparing said data to similar data from said tissue sample obtained either at a different time or at a different location than first said tissue sample, wherein an increase in the number of apoptotic tumor-associated endothelial cells and a decrease in the blood vessel density predicts that said anti-cancer therapy will be therapeutically effective.

2. The method of claim 1, wherein said response to said treatment is determined by comparing said data to a general standard.

3. The method of claim 1, wherein said animal is a human subject.

4. The method of claim 1, wherein said data further comprises the number of apoptotic tumor cells, wherein an increase in the number of apoptosis tumor cells further predicts that said anti-cancer therapy will be therapeutically effective.

5. The method of claim 1, further comprising obtaining data on the number of apoptotic tumor cells, viable endothelial cells, and viable tumor cells.

6. The method of claim 1, wherein said data further comprises cell proliferation in said sample, wherein a decrease in cell proliferation further predicts that said anti-cancer therapy will be therapeutically effective.

7. The method of claim 1, wherein said laser scanning cytometry is automated.

8. The method of claim 1, wherein said data is obtained using an automated analysis technique.

9. The method of claim 8, wherein said automated analysis technique comprises creating a tissue map and selectively gating said tissue map.

10. The method of claim 1, wherein said staining comprises a double-fluorescence labeling technique which comprising a fluorescent marker of apoptosis and a fluorescent endothelial cell antibody on the same tissue sample.

11. The method of claim 10, wherein said fluorescent marker of apoptosis is TdT-dUTP Nick End Labeling (TUNEL).

12. The method of claim 10, wherein said fluorescent marker of apoptosis is fluorescently labeled caspace-3.

13. The method of claim 10, wherein said fluorescent marker for apoptosis is propidium iodide.

14. The method of claim 10, wherein said fluorescent marker for apoptosis is Sytox green.

15. The method of claim 10, wherein said fluorescent endothelial cell antibody is an anti-CD31 or anti-CD34 antibody.

16. The method of claim 10, wherein said fluorescent endothelial cell antibody is labeled with Cy-5.

17. The method of claim 10, wherein said fluorescent endothelial cell antibody comprises a secondary antibody conjugated to a fluorophore.

18. The method of claim 1, wherein subjecting said tissue sample to a laser scanning CYTOMETER comprises contouring cell nuclei and contouring blood vessels.

19. The method of claim 18, wherein contouring of cell nuclei and contouring of blood vessels occur simultaneously.

20. The method of claim 18, wherein contouring of cell nuclei and contouring of blood vessels occur separately.

21. The method of claim 18, further comprising contouring apoptotic endothelial cells.

22. The method of claim 1, further comprising obtaining a sample prior to said anti-cancer therapy.

23. The method of claim 1, further comprising obtaining said sample during said anti-cancer therapy.

24. The method of claim 1, further comprising obtaining said sample after said anti-cancer therapy.

25. The method of claim 24, wherein said sample is obtained less than one hour after treatment.

26. The method of claim 24, wherein said sample is obtained between 1 and 2 hours after treatment.

27. The method of claim 24, wherein said sample is obtained less than 3 hours after treatment.

28. The method of claim 24, wherein said sample is obtained less than 4 hours after treatment.

29. The method of claim 24, wherein said sample is obtained between 4 and 12 hours after treatment.

30. The method of claim 24, wherein said sample is obtained less than 1 day after treatment.

31. The method of claim 24, wherein said sample is obtained less than 3 days after treatment.

32. The method of claim 24, wherein said sample is obtained less than 5 days after treatment.

33. The method of claim 24, wherein said sample is obtained less than 10 days after treatment.

34. The method of claim 24, wherein said sample is obtained less than 15 days after treatment.

35. The method of claim 24, wherein said sample is obtained less than one month after treatment.

36. The method of claim 24, further comprising obtaining between 2 and 50 tissue samples.

37. The method of claim 1, wherein said anti-cancer therapy comprises the use of an anti-angiogenic agent.

38. The method of claim 1, wherein said anti-cancer therapy comprises the use of a chemotherapeutic agent.

39. The method of claim 1, wherein said anti-cancer therapy comprises the use of an radiotherapeutic agent.

40. The method of claim 37, wherein said anti-angiogenic agent is angiostatin.

41. The method of claim 37, wherein said anti-angiogenic agent is endostatin.

42. The method of claim 37, wherein said anti-angiogenic agent is an inhibitor of the receptor for endothelial growth factor.

43. The method of claim 37, wherein said anti-angiogenic agent is VEGF receptor tyrosine kinase inhibitor.

44. The method of claim 1, wherein said patient is has a cancer selected from the group comprising head and neck, brain, lung, liver, spleen, kidney, lymph node, small intestine, pancreas, blood cells, colon, stomach, breast, cervix, bladder, endometrium, prostate, testicle, ovary, skin, esophagus, bone marrow and blood cancer.

45. A kit comprising: a fluorescently-labeled antibody for CD31 or CD34, a fluorescent label for cell nuclei, TAQ polymerase and buffer for use in assessing anti-cancer therapeutic efficacy with laser scanning cytometry.

46. The kit of claim 45, further comprising antigen retrieval buffer.

47. The kit of claim 45, wherein said fluorescent label for endothelial cell markers comprises antibodies for CD31 and CD34.

48. The kit of claim 45, wherein said fluorescent label for fluorescent label for cell nuclei comprises dUTP-FITC.

\* \* \* \* \*

UNITED STATES PATENT AND TRADEMARK OFFICE
CERTIFICATE OF CORRECTION

PATENT NO.        : 8,614,054 B2                                Page 1 of 1
APPLICATION NO.   : 12/024562
DATED             : December 24, 2013
INVENTOR(S)       : Darren W. David et al.

It is certified that error appears in the above-identified patent and that said Letters Patent is hereby corrected as shown below:

In the Claims

In claim 1, column 30, line 16, delete "first said" and replace with --said first-- therefor.

In claim 10, column 30, line 45, delete "which".

In claim 12, column 30, line 52, delete "caspace-3" and replace with --caspase-3-- therefor.

In claim 39, column 32, line 8, delete "an" and replace with --a-- therefor.

In claim 44, column 32, line 17, delete "is".

Signed and Sealed this
Twenty-ninth Day of April, 2014

Michelle K. Lee
*Deputy Director of the United States Patent and Trademark Office*